US007331339B2

(12) United States Patent
Smith et al.

(10) Patent No.: US 7,331,339 B2
(45) Date of Patent: Feb. 19, 2008

(54) METHODS AND SYSTEMS FOR OPERATING AN AEROSOL GENERATOR

(75) Inventors: Niall Smith, Galway (IE); John Power, Galway (IE); James B. Fink, Sunnyvale, CA (US); Michael Klimowicz, Escondido, CA (US)

(73) Assignee: Aerogen, Inc., Mountain View, CA (US)

( * ) Notice: Subject to any disclaimer, the term of this patent is extended or adjusted under 35 U.S.C. 154(b) by 507 days.

(21) Appl. No.: 10/996,994

(22) Filed: Nov. 23, 2004

(65) Prior Publication Data

US 2005/0172954 A1 Aug. 11, 2005

Related U.S. Application Data

(63) Continuation of application No. 10/345,875, filed on Jan. 15, 2003, now Pat. No. 6,968,840, which is a continuation-in-part of application No. 09/849,194, filed on May 4, 2001, now Pat. No. 6,615,824, and a continuation-in-part of application No. 09/812,755, filed on Mar. 20, 2001, now Pat. No. 7,100,600, and a continuation-in-part of application No. 10/284,068, filed on Oct. 30, 2002, said application No. 10/345,875 and a continuation-in-part of application No. 09/876,542, filed on Jun. 7, 2001, now abandoned, and a continuation-in-part of application No. 09/876,402, filed on Jun. 7, 2001, now abandoned, and a continuation-in-part of application No. 09/812,987, filed on Mar. 20, 2001, now Pat. No. 6,948,491.

(60) Provisional application No. 60/408,743, filed on Sep. 5, 2002, provisional application No. 60/439,045, filed on May 20, 2002, provisional application No. 60/381,830, filed on May 20, 2002, provisional application No. 60/380,655, filed on May 14, 2002, provisional application No. 60/349,763, filed on Jan. 15, 2002, provisional application No. 60/349,805, filed on Jan. 15, 2002, provisional application No. 60/344,484, filed on Nov. 1, 2001.

(30) Foreign Application Priority Data

May 5, 2000 (WO) .................. PCT/IE00/00051

(51) Int. Cl.
*A61M 11/00* (2006.01)
(52) U.S. Cl. .................. 128/200.14; 128/200.16; 128/203.15; 128/203.21
(58) Field of Classification Search ........... 128/200.12, 128/200.14, 200.16, 203.21, 200.19, 200.22, 128/200.23, 203.12, 203.14, 203.15
See application file for complete search history.

(56) References Cited

U.S. PATENT DOCUMENTS 550,315 A 11/1895 Allen (Continued)

FOREIGN PATENT DOCUMENTS

CH 477 855 9/1969

(Continued)

OTHER PUBLICATIONS

Abys, J.A. et al., "Annealing Behavior of Palladium-Nickel Alloy Electrodeposits," Plating and Surface Finishing, Aug. 1996, pp. 1-7.
Allen, T. *Particle Size Measurement*, Third Edition, Chapman and Hall pp. 167-169 (1981).

(Continued)

*Primary Examiner*—Steven O. Douglas
(74) *Attorney, Agent, or Firm*—Townsend and Townsend and Crew LLP

(57) ABSTRACT

A nebule comprising at least one identification marker or label can be coupled an aerosol generator. The identification marker can be sensed by a sensing device on the aerosol generator so as to identify the liquid in the nebule to the controller of the aerosol generator. The controller of the aerosol generator can control the aerosol generator based on the information read from the identification marker.

40 Claims, 17 Drawing Sheets

U.S. PATENT DOCUMENTS

| | | | |
|---|---|---|---|
| 809,159 A | 1/1906 | Willis et al. |
| 1,680,616 A | 8/1928 | Horst |
| 2,022,520 A | 11/1935 | Philbrick |
| 2,101,304 A | 12/1937 | Wright |
| 2,158,615 A | 5/1939 | Wright |
| 2,187,528 A | 1/1940 | Wing |
| 2,223,541 A | 12/1940 | Baker |
| 2,266,706 A | 12/1941 | Fox et al. |
| 2,283,333 A | 5/1942 | Martin |
| 2,292,381 A | 8/1942 | Klagges |
| 2,360,297 A | 10/1944 | Wing |
| 2,375,770 A | 5/1945 | Dahlberg |
| 2,383,098 A | 8/1945 | Wheaton |
| 2,404,063 A | 7/1946 | Healy |
| 2,430,023 A | 11/1947 | Longmaid |
| 2,474,996 A | 7/1949 | Wallis |
| 2,512,004 A | 6/1950 | Wing |
| 2,521,657 A | 9/1950 | Severy |
| 2,681,041 A | 6/1954 | Zodtner et al. |
| 2,705,007 A | 3/1955 | Gerber |
| 2,735,427 A | 2/1956 | Sullivan |
| 2,764,946 A | 10/1956 | Henderson |
| 2,764,979 A | 10/1956 | Henderson |
| 2,779,623 A | 1/1957 | Eisenkraft |
| 2,935,970 A | 5/1960 | Morse et al. |
| 3,103,310 A | 9/1963 | Lang |
| 3,325,031 A | 6/1967 | Singier |
| 3,411,854 A | 11/1968 | Rosler et al. |
| 3,515,348 A | 6/1970 | Coffman, Jr. |
| 3,550,864 A | 12/1970 | East |
| 3,558,052 A | 1/1971 | Dunn |
| 3,561,444 A | 2/1971 | Boucher |
| 3,563,415 A | 2/1971 | Ogle |
| 3,680,954 A | 8/1972 | Frank |
| 3,719,328 A | 3/1973 | Hindman |
| 3,738,574 A | 6/1973 | Guntersdorfer et al. |
| 3,771,982 A | 11/1973 | Dobo |
| 3,790,079 A | 2/1974 | Berglund et al. |
| 3,804,329 A | 4/1974 | Martner |
| 3,812,854 A | 5/1974 | Michaels et al. |
| 3,838,686 A | 10/1974 | Szekely |
| 3,842,833 A | 10/1974 | Ogle |
| 3,865,106 A | 2/1975 | Palush |
| 3,903,884 A | 9/1975 | Huston et al. |
| 3,906,950 A | 9/1975 | Cocozza |
| 3,908,654 A | 9/1975 | Lhoest et al. |
| 3,950,760 A | 4/1976 | Rauch et al. |
| 3,951,313 A | 4/1976 | Coniglione |
| 3,958,249 A | 5/1976 | DeMaine et al. |
| 3,970,250 A | 7/1976 | Drews |
| 3,983,740 A | 10/1976 | Danel |
| 3,993,223 A | 11/1976 | Welker, III et al. |
| 4,005,435 A | 1/1977 | Lundquist et al. |
| 4,030,492 A | 6/1977 | Simburner |
| 4,052,986 A | 10/1977 | Scaife |
| 4,059,384 A | 11/1977 | Holland et al. |
| D246,574 S | 12/1977 | Meierhoefer |
| 4,076,021 A | 2/1978 | Thompson |
| 4,083,368 A | 4/1978 | Freezer |
| 4,094,317 A | 6/1978 | Wasnich |
| 4,101,041 A | 7/1978 | Mauro, Jr. et al. |
| 4,106,503 A | 8/1978 | Rsenthal et al. |
| 4,109,174 A | 8/1978 | Hodgson |
| 4,113,809 A | 9/1978 | Abair et al. |
| D249,958 S | 10/1978 | Meierhoefer |
| 4,119,096 A | 10/1978 | Drews |
| 4,121,583 A | 10/1978 | Chen |
| 4,159,803 A | 7/1979 | Cameto et al. |
| 4,207,990 A | 6/1980 | Weiler et al. |
| 4,210,155 A | 7/1980 | Grimes |
| 4,226,236 A | 10/1980 | Genese |
| 4,240,081 A | 12/1980 | Devitt |
| 4,240,417 A | 12/1980 | Holever |
| 4,248,227 A | 2/1981 | Thomas |
| 4,261,512 A | 4/1981 | Zierenberg |
| D259,213 S | 5/1981 | Pagels |
| 4,268,460 A | 5/1981 | Boiarski et al. |
| 4,294,407 A | 10/1981 | Reichl et al. |
| 4,298,045 A | 11/1981 | Weiler et al. |
| 4,299,784 A | 11/1981 | Hense |
| 4,300,546 A | 11/1981 | Kruber |
| 4,301,093 A | 11/1981 | Eck |
| 4,319,155 A | 3/1982 | Makai et al. |
| 4,334,531 A | 6/1982 | Reichl et al. |
| 4,336,544 A | 6/1982 | Donald et al. |
| 4,338,576 A | 7/1982 | Takahashi et al. |
| 4,368,476 A | 1/1983 | Uehara et al. |
| 4,368,850 A | 1/1983 | Szekely |
| 4,374,707 A | 2/1983 | Pollack |
| 4,389,071 A | 6/1983 | Johnson, Jr. et al. |
| 4,408,719 A | 10/1983 | Last |
| 4,428,802 A | 1/1984 | Kanai et al. |
| 4,431,136 A | 2/1984 | Janner et al. |
| 4,454,877 A | 6/1984 | Miller et al. |
| 4,465,234 A | 8/1984 | Maehara et al. |
| 4,474,251 A | 10/1984 | Johnson, Jr. |
| 4,474,326 A | 10/1984 | Takahashi |
| 4,475,113 A | 10/1984 | Lee et al. |
| 4,479,609 A | 10/1984 | Maeda et al. |
| 4,512,341 A | 4/1985 | Lester |
| 4,530,464 A | 7/1985 | Yamamoto et al. |
| 4,533,082 A | 8/1985 | Maehara et al. |
| 4,539,575 A | 9/1985 | Nilsson |
| 4,544,933 A | 10/1985 | Heinzl |
| 4,546,361 A | 10/1985 | Brescia et al. |
| 4,550,325 A | 10/1985 | Viola |
| 4,566,452 A | 1/1986 | Farr |
| 4,591,883 A | 5/1986 | Isayama |
| 4,593,291 A | 6/1986 | Howkins |
| 4,605,167 A | 8/1986 | Maehara |
| 4,613,326 A | 9/1986 | Szwarc |
| 4,620,201 A | 10/1986 | Heinzl et al. |
| 4,628,890 A | 12/1986 | Freeman |
| 4,632,311 A | 12/1986 | Nakane et al. |
| 4,658,269 A | 4/1987 | Rezanka |
| 4,659,014 A | 4/1987 | Soth et al. |
| 4,677,975 A | 7/1987 | Edgar et al. |
| 4,678,680 A | 7/1987 | Abowitz |
| 4,679,551 A | 7/1987 | Anthony |
| 4,681,264 A | 7/1987 | Johnson, Jr. |
| 4,693,853 A | 9/1987 | Falb et al. |
| 4,702,418 A | 10/1987 | Carter et al. |
| 4,722,906 A | 2/1988 | Guire |
| 4,753,579 A | 6/1988 | Murphy |
| 4,790,479 A | 12/1988 | Matsumoto et al. |
| 4,793,339 A | 12/1988 | Matsumoto et al. |
| 4,796,807 A | 1/1989 | Bendig et al. |
| 4,799,622 A | 1/1989 | Ishikawa et al. |
| 4,805,609 A | 2/1989 | Roberts et al. |
| 4,819,629 A | 4/1989 | Jonson |
| 4,819,834 A | 4/1989 | Thiel |
| 4,826,080 A | 5/1989 | Ganser |
| 4,826,759 A | 5/1989 | Guire et al. |
| 4,828,886 A | 5/1989 | Hieber |
| 4,843,445 A | 6/1989 | Stemme |
| 4,849,303 A | 7/1989 | Graham et al. |
| 4,850,534 A | 7/1989 | Takahashi et al. |
| 4,865,006 A | 9/1989 | Nogi et al. |
| 4,871,489 A | 10/1989 | Ketcham |
| 4,872,553 A | 10/1989 | Suzuki et al. |
| 4,877,989 A | 10/1989 | Drews et al. |
| 4,888,516 A | 12/1989 | Daeges et al. |
| 4,922,901 A | 5/1990 | Brooks et al. |
| 4,926,915 A | 5/1990 | Deussen et al. |

| Patent No. | Date | Inventor |
|---|---|---|
| 4,934,358 A | 6/1990 | Nilsson et al. |
| 4,954,225 A | 9/1990 | Bakewell |
| 4,957,239 A | 9/1990 | Tempelman |
| 4,964,521 A | 10/1990 | Wieland et al. |
| D312,209 S | 11/1990 | Morrow et al. |
| 4,968,299 A | 11/1990 | Ahlstrand et al. |
| 4,971,665 A | 11/1990 | Sexton |
| 4,973,493 A | 11/1990 | Guire |
| 4,976,259 A | 12/1990 | Higson et al. |
| 4,979,959 A | 12/1990 | Guire |
| 4,994,043 A | 2/1991 | Ysebaert |
| 5,002,048 A | 3/1991 | Makiej, Jr. |
| 5,002,582 A | 3/1991 | Guire et al. |
| 5,007,419 A | 4/1991 | Weinstein et al. |
| 5,016,024 A | 5/1991 | Lam et al. |
| 5,021,701 A | 6/1991 | Takahashi et al. |
| 5,022,587 A | 6/1991 | Hochstein |
| 5,024,733 A | 6/1991 | Abys et al. |
| 5,046,627 A | 9/1991 | Hansen |
| 5,062,419 A | 11/1991 | Rider |
| 5,063,396 A | 11/1991 | Shiokawa et al. |
| 5,063,922 A | 11/1991 | Häkkinen |
| 5,073,484 A | 12/1991 | Swanson et al. |
| 5,076,266 A | 12/1991 | Babaev |
| 5,080,093 A | 1/1992 | Raabe et al. |
| 5,080,649 A | 1/1992 | Vetter |
| 5,086,765 A | 2/1992 | Levine |
| 5,086,785 A | 2/1992 | Gentile et al. |
| 5,115,803 A | 5/1992 | Sioutas |
| 5,115,971 A | 5/1992 | Greenspan et al. |
| D327,008 S | 6/1992 | Friedman |
| 5,122,116 A | 6/1992 | Kriesel et al. |
| 5,129,579 A | 7/1992 | Conte |
| 5,134,993 A | 8/1992 | Van Der Linden et al. |
| 5,139,016 A | 8/1992 | Waser |
| 5,140,740 A | 8/1992 | Weigelt |
| 5,147,073 A | 9/1992 | Cater |
| 5,152,456 A | 10/1992 | Ross et al. |
| 5,157,372 A | 10/1992 | Langford |
| 5,164,740 A | 11/1992 | Ivri |
| 5,169,029 A | 12/1992 | Behar et al. |
| 5,170,782 A | 12/1992 | Kocinski |
| 5,180,482 A | 1/1993 | Abys et al. |
| 5,186,164 A | 2/1993 | Raghuprasad |
| 5,186,166 A | 2/1993 | Riggs et al. |
| 5,198,157 A | 3/1993 | Bechet |
| 5,201,322 A | 4/1993 | Henry et al. |
| 5,213,860 A | 5/1993 | Laing |
| 5,217,148 A | 6/1993 | Cater |
| 5,217,492 A | 6/1993 | Guire et al. |
| 5,227,168 A | 7/1993 | Chvapil |
| 5,230,496 A | 7/1993 | Shillington et al. |
| 5,245,995 A | 9/1993 | Sullivan et al. |
| 5,248,087 A | 9/1993 | Dressler |
| 5,258,041 A | 11/1993 | Guire et al. |
| 5,261,601 A | 11/1993 | Ross et al. |
| 5,263,992 A | 11/1993 | Guire |
| 5,279,568 A | 1/1994 | Cater |
| 5,297,734 A | 3/1994 | Toda |
| 5,299,739 A | 4/1994 | Takahashi et al. |
| 5,303,854 A | 4/1994 | Cater |
| 5,309,135 A | 5/1994 | Langford |
| 5,312,281 A | 5/1994 | Takahashi et al. |
| 5,313,955 A | 5/1994 | Rodder |
| 5,319,971 A | 6/1994 | Osswald et al. |
| 5,320,603 A | 6/1994 | Vetter et al. |
| 5,322,057 A | 6/1994 | Raabe et al. |
| 5,342,011 A | 8/1994 | Short |
| 5,342,504 A | 8/1994 | Hirano et al. |
| 5,347,998 A | 9/1994 | Hodson et al. |
| 5,348,189 A | 9/1994 | Cater |
| 5,350,116 A | 9/1994 | Cater |
| 5,355,872 A | 10/1994 | Riggs et al. |
| 5,357,946 A | 10/1994 | Kee et al. |
| 5,372,126 A | 12/1994 | Blau |
| 5,383,906 A | 1/1995 | Burchett et al. |
| 5,388,571 A | 2/1995 | Roberts et al. |
| 5,392,769 A | 2/1995 | Johansson et al. |
| 5,396,883 A | 3/1995 | Knupp et al. |
| 5,414,075 A | 5/1995 | Swan et al. |
| 5,415,161 A | 5/1995 | Ryder |
| 5,419,315 A | 5/1995 | Rubsamen |
| 5,426,458 A | 6/1995 | Wenzel et al. |
| 5,431,155 A | 7/1995 | Marelli |
| 5,435,282 A | 7/1995 | Haber et al. |
| 5,435,297 A | 7/1995 | Klein |
| 5,437,267 A | 8/1995 | Weinstein et al. |
| 5,445,141 A | 8/1995 | Kee et al. |
| D362,390 S | 9/1995 | Weiler |
| 5,449,502 A | 9/1995 | Igusa et al. |
| 5,452,711 A | 9/1995 | Gault |
| 5,458,135 A | 10/1995 | Patton et al. |
| 5,458,289 A | 10/1995 | Cater |
| 5,474,059 A | 12/1995 | Cooper |
| 5,477,992 A | 12/1995 | Jinks et al. |
| 5,479,920 A | 1/1996 | Piper et al. |
| 5,487,378 A | 1/1996 | Robertson et al. |
| 5,489,266 A | 2/1996 | Grimard |
| 5,497,944 A | 3/1996 | Weston et al. |
| D369,212 S | 4/1996 | Snell |
| 5,511,726 A | 4/1996 | Greenspan et al. |
| 5,512,329 A | 4/1996 | Guire et al. |
| 5,512,474 A | 4/1996 | Clapper et al. |
| 5,515,841 A | 5/1996 | Robertson et al. |
| 5,515,842 A | 5/1996 | Ramseyer et al. |
| 5,516,043 A | 5/1996 | Manna et al. |
| 5,518,179 A | 5/1996 | Humberstone et al. |
| 5,529,055 A | 6/1996 | Gueret |
| 5,533,497 A | 7/1996 | Ryder |
| 5,542,410 A | 8/1996 | Goodman et al. |
| 5,549,102 A | 8/1996 | Lintl et al. |
| 5,560,837 A | 10/1996 | Trueba |
| 5,563,056 A | 10/1996 | Swan et al. |
| D375,352 S | 11/1996 | Bologna |
| 5,579,757 A | 12/1996 | McMahon et al. |
| 5,582,330 A | 12/1996 | Iba |
| 5,584,285 A | 12/1996 | Salter et al. |
| 5,586,550 A | 12/1996 | Ivri et al. |
| 5,588,166 A | 12/1996 | Burnett |
| 5,601,077 A | 2/1997 | Imbert |
| 5,609,798 A | 3/1997 | Liu et al. |
| 5,632,878 A | 5/1997 | Kitano |
| 5,635,096 A | 6/1997 | Singer et al. |
| 5,637,460 A | 6/1997 | Swan et al. |
| 5,647,349 A | 7/1997 | Ohki et al. |
| 5,653,227 A | 8/1997 | Barnes et al. |
| 5,654,007 A | 8/1997 | Johnson et al. |
| 5,654,162 A | 8/1997 | Guire et al. |
| 5,654,460 A | 8/1997 | Rong |
| 5,657,926 A | 8/1997 | Toda |
| 5,660,166 A | 8/1997 | Lloyd |
| 5,664,557 A | 9/1997 | Makiej, Jr. |
| 5,664,706 A | 9/1997 | Cater |
| 5,665,068 A | 9/1997 | Takamura |
| 5,666,946 A | 9/1997 | Langenback |
| 5,670,999 A | 9/1997 | Takeuchi et al. |
| 5,685,491 A | 11/1997 | Marks et al. |
| 5,692,644 A | 12/1997 | Gueret |
| 5,707,818 A | 1/1998 | Chudzik et al. |
| 5,709,202 A | 1/1998 | Lloyd et al. |
| 5,714,360 A | 2/1998 | Swan et al. |
| 5,714,551 A | 2/1998 | Bezwada et al. |
| 5,718,222 A | 2/1998 | Lloyd et al. |
| D392,184 S | 3/1998 | Weiler |
| 5,724,957 A | 3/1998 | Rubsamen et al. |
| 5,744,515 A | 4/1998 | Clapper |

| | | | | | |
|---|---|---|---|---|---|
| 5,752,502 A | 5/1998 | King | 6,269,810 B1 | 8/2001 | Brooker et al. |
| 5,755,218 A | 5/1998 | Johansson et al. | 6,270,473 B1 | 8/2001 | Schwebel |
| 5,758,637 A | 6/1998 | Ivri et al. | 6,273,342 B1 | 8/2001 | Terada et al. |
| 5,775,506 A | 7/1998 | Grabenkort | 6,318,640 B1 | 11/2001 | Coffee |
| 5,788,665 A | 8/1998 | Sekins | 6,328,030 B1 | 12/2001 | Kidwell et al. |
| 5,788,819 A | 8/1998 | Onishi et al. | 6,328,033 B1 | 12/2001 | Avrahami |
| 5,790,151 A | 8/1998 | Mills | 6,341,732 B1 | 1/2002 | Martin et al. |
| 5,810,004 A | 9/1998 | Ohki et al. | 6,358,058 B1 | 3/2002 | Strupat et al. |
| 5,819,730 A | 10/1998 | Stone et al. | 6,394,363 B1 | 5/2002 | Arnott et al. |
| 5,823,179 A | 10/1998 | Grychowski et al. | 6,402,046 B1 | 6/2002 | Loser |
| 5,823,428 A | 10/1998 | Humberstone et al. | 6,405,934 B1 | 6/2002 | Hess et al. |
| 5,829,723 A | 11/1998 | Brunner et al. | 6,427,682 B1 | 8/2002 | Klimowicz et al. |
| 5,836,515 A | 11/1998 | Fonzes | 6,443,146 B1 | 9/2002 | Voges |
| 5,839,617 A | 11/1998 | Cater et al. | 6,443,366 B1 | 9/2002 | Hirota et al. |
| 5,842,468 A | 12/1998 | Denyer et al. | 6,467,476 B1 | 10/2002 | Ivri et al. |
| 5,862,802 A | 1/1999 | Bird | 6,530,370 B1 | 3/2003 | Heinonen |
| 5,865,171 A | 2/1999 | Cinquin | 6,540,153 B1 | 4/2003 | Ivri |
| 5,878,900 A | 3/1999 | Hansen | 6,540,154 B1 | 4/2003 | Ivri et al. |
| 5,893,515 A | 4/1999 | Hahn et al. | 6,543,443 B1 | 4/2003 | Klimowicz et al. |
| 5,894,841 A | 4/1999 | Voges | 6,546,927 B2 | 4/2003 | Litherland et al. |
| 5,897,008 A | 4/1999 | Hansen | 6,550,472 B2 | 4/2003 | Litherland et al. |
| 5,910,698 A | 6/1999 | Yagi | 6,554,201 B2 | 4/2003 | Klimowicz et al. |
| 5,915,377 A | 6/1999 | Coffee | 6,581,595 B1 | 6/2003 | Murdock et al. |
| 5,918,637 A | 7/1999 | Fleischman | 6,615,824 B2 | 9/2003 | Power |
| 5,925,019 A | 7/1999 | Ljungquist | 6,629,646 B1 | 10/2003 | Ivri |
| 5,938,117 A | 8/1999 | Ivri | 6,640,804 B2 | 11/2003 | Ivri |
| 5,950,619 A | 9/1999 | Van Der Linden et al. | 6,651,650 B1 | 11/2003 | Yamamoto et al. |
| 5,954,268 A | 9/1999 | Joshi et al. | 6,705,315 B2 | 3/2004 | Sullivan et al. |
| 5,960,792 A | 10/1999 | Lloyd et al. | 6,732,944 B2 | 5/2004 | Litherland et al. |
| 5,964,417 A | 10/1999 | Amann et al. | 6,745,768 B2 | 6/2004 | Colla et al. |
| 5,970,974 A | 10/1999 | Van Der Linden et al. | 6,745,770 B2 | 6/2004 | McAuliffe et al. |
| 5,976,344 A | 11/1999 | Abys et al. | 6,755,189 B2 | 6/2004 | Ivri et al. |
| 5,993,805 A | 11/1999 | Sutton et al. | 6,769,626 B1 | 8/2004 | Haveri |
| 6,000,396 A | 12/1999 | Melker et al. | 6,782,886 B2 | 8/2004 | Narayan et al. |
| 6,007,518 A | 12/1999 | Kriesel et al. | 6,810,876 B2 | 11/2004 | Berthon-Jones |
| 6,012,450 A | 1/2000 | Rubsamen | 6,814,071 B2 | 11/2004 | Klimowicz et al. |
| 6,014,970 A | 1/2000 | Ivri et al. | 6,817,361 B2 | 11/2004 | Berthon-Jones et al. |
| 6,026,809 A | 2/2000 | Abrams et al. | 6,840,240 B1 | 1/2005 | Berthon-Jones et al. |
| 6,029,666 A | 2/2000 | Aloy et al. | 6,845,770 B2 | 1/2005 | Klimowicz et al. |
| 6,032,665 A | 3/2000 | Psaros | 6,851,626 B2 | 2/2005 | Patel et al. |
| 6,037,587 A | 3/2000 | Dowell et al. | 6,860,268 B2 | 3/2005 | Bohn et al. |
| 6,039,696 A | 3/2000 | Bell | 2001/0013554 A1 | 8/2001 | Borland et al. |
| 6,045,215 A | 4/2000 | Coulman | 2001/0015737 A1 | 8/2001 | Truninger et al. |
| 6,045,874 A | 4/2000 | Himes | 2002/0011247 A1 | 1/2002 | Ivri et al. |
| 6,047,818 A | 4/2000 | Warby et al. | 2002/0023650 A1 | 2/2002 | Gunaratnam et al. |
| 6,055,869 A | 5/2000 | Stemme et al. | 2002/0033178 A1 | 3/2002 | Farrell et al. |
| 6,060,128 A | 5/2000 | Kim et al. | 2002/0036601 A1 | 3/2002 | Puckeridge et al. |
| 6,062,212 A | 5/2000 | Davison et al. | 2002/0078958 A1 | 6/2002 | Stenzler |
| 6,068,148 A | 5/2000 | Weiler | 2002/0104530 A1 | 8/2002 | Ivri et al. |
| 6,085,740 A | 7/2000 | Ivri et al. | 2002/0121274 A1 | 9/2002 | Borland et al. |
| 6,096,011 A | 8/2000 | Trombley, III et al. | 2002/0134372 A1 | 9/2002 | Loeffler et al. |
| 6,105,877 A | 8/2000 | Coffee | 2002/0134374 A1 | 9/2002 | Loeffler et al. |
| 6,106,504 A | 8/2000 | Urrutia | 2002/0134375 A1 | 9/2002 | Loeffler et al. |
| 6,116,234 A | 9/2000 | Genova et al. | 2002/0134377 A1 | 9/2002 | Loeffler et al. |
| 6,123,413 A | 9/2000 | Agarwal et al. | 2002/0162551 A1 | 11/2002 | Litherland |
| 6,139,674 A | 10/2000 | Markham et al. | 2003/0140921 A1 | 7/2003 | Smith et al. |
| 6,142,146 A | 11/2000 | Abrams et al. | 2003/0145859 A1 | 8/2003 | Bohn et al. |
| 6,145,963 A | 11/2000 | Pidwerbecki et al. | 2003/0150445 A1 | 8/2003 | Power et al. |
| 6,146,915 A | 11/2000 | Pidwerbecki et al. | 2003/0150446 A1 | 8/2003 | Patel et al. |
| 6,152,130 A | 11/2000 | Abrams et al. | 2003/0226906 A1 | 12/2003 | Ivri |
| 6,155,676 A | 12/2000 | Etheridge et al. | 2004/0000598 A1 | 1/2004 | Ivri |
| 6,158,431 A | 12/2000 | Poole | 2004/0004133 A1 | 1/2004 | Ivri et al. |
| 6,161,536 A | 12/2000 | Redmon et al. | 2004/0011358 A1 | 1/2004 | Smaldone et al. |
| 6,163,588 A | 12/2000 | Matsumoto et al. | 2004/0035413 A1 | 2/2004 | Smaldone et al. |
| 6,182,662 B1 | 2/2001 | McGhee | 2004/0035490 A1 | 2/2004 | Power |
| 6,186,141 B1 | 2/2001 | Pike et al. | 2004/0050947 A1 | 3/2004 | Power et al. |
| 6,196,218 B1 | 3/2001 | Voges | 2004/0139963 A1 | 7/2004 | Ivri et al. |
| 6,196,219 B1 | 3/2001 | Hess et al. | 2004/0139968 A1 | 7/2004 | Loeffler et al. |
| 6,205,999 B1 | 3/2001 | Ivri et al. | 2004/0188534 A1 | 9/2004 | Litherland et al. |
| 6,216,916 B1 | 4/2001 | Maddox et al. | 2004/0194783 A1 | 10/2004 | McAuliffe et al. |
| 6,223,746 B1 | 5/2001 | Jewett et al. | 2004/0226561 A1 | 11/2004 | Colla et al. |
| 6,235,177 B1 | 5/2001 | Borland et al. | 2004/0226566 A1 | 11/2004 | Gunaratnam et al. |
| 6,254,219 B1 | 7/2001 | Agarwal et al. | 2004/0256488 A1 | 12/2004 | Loeffler et al. |

2005/0011514 A1 1/2005 Power et al.

FOREIGN PATENT DOCUMENTS

| CH | 555 681 | | 11/1974 |
|---|---|---|---|
| DE | 11 03 522 | | 3/1961 |
| EP | 0 049 636 | A1 | 4/1982 |
| EP | 0 103 161 | A2 | 3/1984 |
| EP | 0 134 847 | A1 | 3/1985 |
| EP | 0 178 925 | A2 | 4/1986 |
| EP | 0 387 222 | A1 | 9/1990 |
| EP | 0 432 992 | A1 | 6/1991 |
| EP | 0 476 991 | B1 | 3/1992 |
| EP | 0 480 615 | A1 | 4/1992 |
| EP | 0 510 648 | A2 | 10/1992 |
| EP | 0 516 565 | A1 | 12/1992 |
| EP | 0 542 723 | A2 | 5/1993 |
| EP | 0 933 138 | A2 | 4/1999 |
| EP | 0 923 957 | A1 | 6/1999 |
| EP | 1 142 600 | A1 | 10/2001 |
| GB | 973 458 | | 10/1964 |
| GB | 1 454 597 | | 11/1976 |
| GB | 2 073 616 | A | 10/1981 |
| GB | 2 101 500 | | 1/1983 |
| GB | 2 177 623 | A | 1/1987 |
| GB | 2 240 494 | A | 7/1991 |
| GB | 2 272 389 | A | 5/1994 |
| JP | 57-023852 | | 2/1982 |
| JP | 57-105608 | | 7/1982 |
| JP | 58-061857 | | 4/1983 |
| JP | 58-139757 | | 8/1983 |
| JP | 59-142162 | A | 8/1984 |
| JP | 60-004714 | | 1/1985 |
| JP | 61-008357 | A | 1/1986 |
| JP | 61-215059 | A | 9/1986 |
| JP | 02-135169 | | 5/1990 |
| JP | 02-189161 | | 7/1990 |
| JP | 60-07721 | A | 1/1994 |
| WO | WO 82/03548 | A | 10/1982 |
| WO | WO 92/07600 | A1 | 5/1992 |
| WO | WO 92/11050 | A1 | 9/1992 |
| WO | WO 92/17231 | A1 | 10/1992 |
| WO | WO 93/01404 | A1 | 1/1993 |
| WO | WO 93/10910 | A1 | 6/1993 |
| WO | WO 94/09912 | A1 | 5/1994 |
| WO | WO 96/09229 | | 3/1996 |
| WO | WO 99/17888 | | 4/1999 |
| WO | WO 00/37132 | | 6/2000 |

OTHER PUBLICATIONS

Ashgriz, N. et al. "Development of a Controlled Spray Generator" Rev. Sci. Instrum., 1987, pp. 1291-1296, vol. 58, No. 7.

Berggren, E. "Pilot Study of Nebulized Surfactant Therapy for Neonatal Respiratory Distress Syndrome", Acta Paediatr 89: 460-464, Taylor & Francis, ISSN 0803-5253, 2000, Sweden.

Berglund, R.N., et al. "Generation of Monodisperse Aerosol Standards" Environ. Sci. Technology, Feb. 1973, pp. 147-153, vol. 7, No. 2.

Cipolla, D.C. et al., "Assessment of Aerosol Delivery Systems for Recombinant Human Deoxyribonuclease," S.T.P. Pharma Sciences 4 (1) 50-62, 1994.

Cipolla, D.C. et al., "Characterization of Aerosols of Human Recombinant Deoxyribonuclease I (rhDNase) Generated by neulizers," Pharmaceutical Research II(4) 491-498, 1994.

Dogan, Aydin PhD, Thesis: "Flexible Moonie and Cymbal' Actuators", Penn State University, 1994.

Duarte, Alexander G. et al. "Inhalation Therapy During Mechanical Ventilation" Respiratory Care Clinics of North America, Aerosol Therapy, Jun. 2001, pp. 233-259, vol. 7, No. 2.

Fink, James B. et al. "Aerosol Drug Therapy," Clinical Practice in Respiratory Care; Chapter 12, pp. 308-342; 1999.

Fink, James B. et al. "Aerosol Therapy in Mechanically Ventilated Patients: Recent Advances and New Techniques" Seminars in Respiratory and Critical Care Medicine, 2000, pp. 183-201, vol. 21, No. 3.

Fink, James B. et al. Diagram from and abstract of article entitled "Optimizing efficiency of nebulizers during mechanical ventilation: The effect of placement and type of ventilator circuit" Chest, Oct. 1999, 116:312S.

Gaiser Tool Company catalog, pp. 26, 29-30 (1990).

Gonda, I. "Therapeutic Aerosols," Pharmaceutics, The Science of Dosage Form Design, Editor: M.E. Aulton, 341-358, 1988.

Hancock, B.C. et al., "Molecular Mobility of Amorphous Pharmaceutical Solids Below Their Glass Transition Temperatures," Pharmaceutical Research 12, 799-806 (1995).

Heyder, J. et al., "Deposition of particles in the human respiratory tract in the size range 0.005-15 microns." J Aerosol Sci 17: 811-825, 1986.

Hickey, Anthony J. "Pharmaceutical Inhalation Aerosol Technology," Drugs And The Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Jorch, G. Letter to the Editor, "Surfactant Aerosol Treatment of Respiratory Distress Syndrome in Spontaneously Breathing Premature Infants", Pediatric Pulmonology 24: 222-224, 1997, Wiley-Liss.

Maehara, N. et al. "Atomizing rate control of a multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876, vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikai Gakkai Zenkoku Taikai Koenkai Koen Ronbunshu 69:660-662 (1991).

Palla Tech Pd an Pd Alloy Processes—Procedure for the Analysis of Additive IVS in Palla Tech Plating Solutions by HPLC, Technical Bulletin, Electroplating Chemicals & Services, 029-A, Lucent Technologies,, pp. 1-5, 1996.

Siemens, "Servo Ultra Nebulizer 345 Operating Manual," pp. 1-23.

Smaldone, G. C. "Aerosolized Antibiotics: Current and Future", Respiratory Care, 2000, vol. 45, No. 6, pp. 667-675.

Smedsaas-Löfvenbert, A. "Nebulization of Drugs in a Nasal CPAP System", Scandinavian University Press, 1999, Acta Paediatr 88: 89-92, Sweden.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6, 1.

Wehl, Wolfgang R. "Ink-Jet Printing: The Present State of the Art" for Siemens AG, 1989.

- Providing an Aerosol Generator — 100
- Coupling a Nebule to an Interface of the Aerosol Generator — 102
- Reading an Identification Marker on the Nebule — 104
- Operating the Aerosol Generator According to an Operation Program Based on the Information Read from the Identification Marker — 106

Fig. 12

- Providing a Nebulizer System — 110
- Providing a Nebule Having a Key Element — 112
- Inserting the Nebule into A Housing of the Nebulizer System, wherein the Key Element Provides Access to a Reservoir of the Nebulizer System When Properly Keyed with the Housing — 114
- Transferring Liquid from the Nebule Into the Reservoir — 116
- Operating the Aerosol Generator to Aerosolize the Liquid — 118

```
                                    ┌─────────────────┐
                                    │  Providing an   │─130
                                    │    Aerosol      │
                                    │   Generator     │
                                    └────────┬────────┘
                                             │
                                    ┌────────┴────────┐
                                    │ Coupling a Nebule to │─132
                                    │ an Interface of the  │
                                    │  Aerosol Generator   │
                                    └────────┬────────┘
┌───────────────────┐                        │
│ Taking One or More│─120           ┌────────┴────────┐
│     Breaths       │               │ Reading an      │─134
└─────────┬─────────┘               │ Identification  │
          │                         │ Marker on the   │
┌─────────┴─────────┐               │    Nebule       │
│    Measuring      │─122           └────────┬────────┘
│ Characteristics   │                        │
│   of the Breath   │               ┌────────┴────────┐
└─────────┬─────────┘               │ Delivering a    │─136
          │                         │ Fluid from the  │
┌─────────┴─────────┐               │ Nebule to the   │
│ Taking Another    │               │ Aerosol Gen.    │
│ Breath and        │               └────────┬────────┘
│ Operating an      │                        │
│ Aerosol Generator │               ┌────────┴────────┐
│ Based on the      │               │   Measuring     │─138
│ Measured          │               │   Breathing     │
│ Characteristics   │               │ Characteristics │
│ of the Breath     │               │ of the Patient's│
└───────────────────┘               │     Breath      │
                 │─124              └────────┬────────┘
                                             │
                                    ┌────────┴────────┐
        Fig. 13                     │ Operating the   │─140
                                    │ Aerosol Gen.    │
                                    │ based on the    │
                                    │ Info Read from  │
                                    │ Identification  │
                                    │ Marker and the  │
                                    │ Measured        │
                                    │ Breathing       │
                                    │ Characteristics │
                                    └─────────────────┘

Fig. 14
```

Fig. 15a
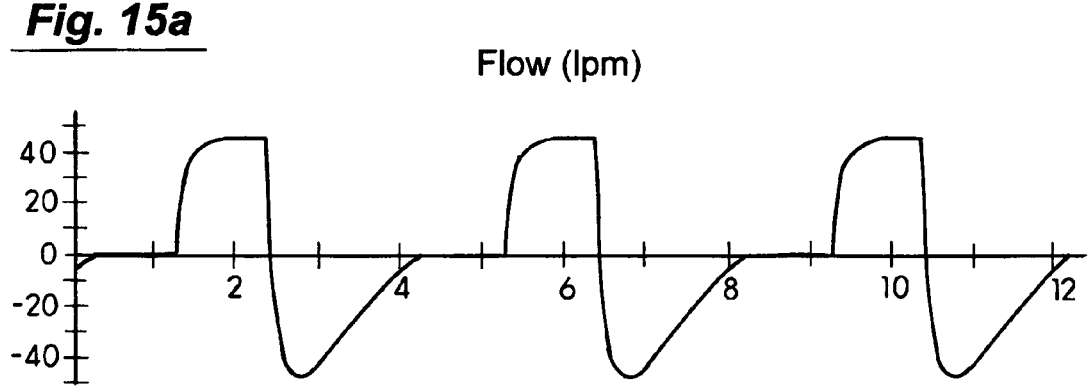
Fig. 15b
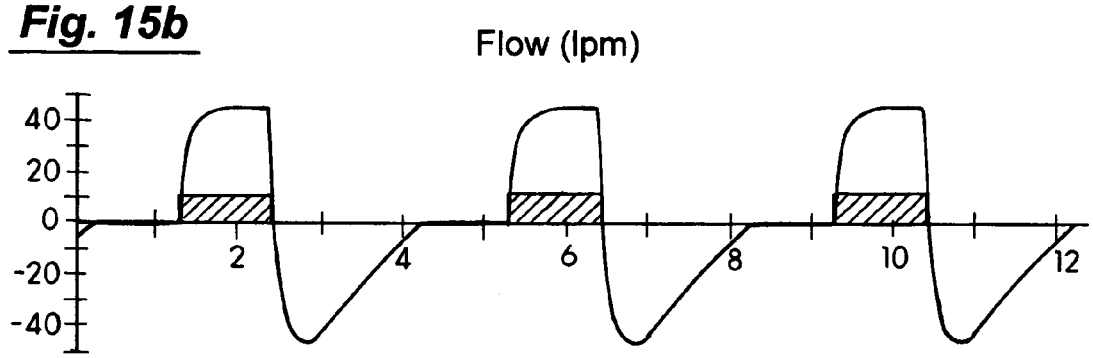
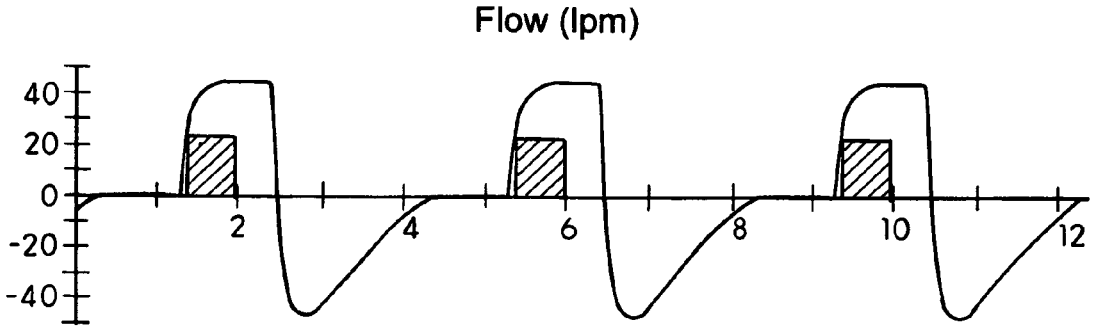
Fig. 15c

Fig. 18

```
                    200
                   /
        ┌─────────────────┐
        │ select regime   │
        │ for aerosol     │
        │ generation      │
        └─────────────────┘
         ↙       ↓       ↘
┌──────────────┐      ┌──────────────┐
│ regime I     │      │ regime II    │
│ continuous   │      │ - for entire │
│ aerosol      │      │ inhalation   │
│ generation   │      │ phase        │
└──────────────┘      └──────────────┘
   202                    204
```

- 200 select regime for aerosol generation
- 202 regime I — continuous aerosol generation
- 204 regime II — for entire inhalation phase
- 206 set aerosol generation to begin upon commencement of inhalation phase
- 208 set aerosol generation to stop upon ending of inhalation phase
- 210 begin aerosol generation at the start of the inhalation phase
- 212 end of inhalation phase
- 214 stop aerosol generation until next cycle
- 216 regime III — during a predetermined percentage of inhalation phase
- 218 set a first predetermined point during inhalation - to start aerosolization
- 220 set a second predetermined point during inhalation - to start aerosolization
- 222 begin aerosol generation at the first predetermined point
- 224 second predetermined point reached

- 250: selection of a regime for administration of aerosol
- 252: aerosol generator controller selects operation sequence based on selected regime
- 254: controller receives signal indicating that ventilator has begun to supply an inhalation phase
- 256: controller carries out selected operation sequence
- 258 (regime II): controller turns on aerosol generator upon commencement of inhalation phase provided by the ventilator
- 260: inhalation phase completed
- 262: controller turns off aerosol generator
- 264 (regimes III and IV): predetermined point at which predetermined % inhalation phase completed
- 266: controller turns on aerosol generator
- 268 (regime III): predetermined % inhalation phase completed
- 270 (regime IV): predetermined point may be after exhalation has begun after inhalation
- 272: controller turns on aerosol generator
- 274: at a predetermined point after completion of inhalation phase and...
- 276 (regime IVa): ...prior to next inhalation
- 278 (regime IVb): ...at the start of next inhalation phase
- 280 (regime IVc): ...after start of next inhalation phase
- 282: predetermined % of next inhalation phase completed

METHODS AND SYSTEMS FOR OPERATING AN AEROSOL GENERATOR

CROSS-REFERENCES TO RELATED APPLICATIONS

The present application is a continuation of U.S. patent application Ser. No. 10/345,875 (now issued as U.S. Pat. No. 6,968,840), filed Jan. 15, 2003, which is:

1) a continuation-in-part of U.S. patent application Ser. No. 09/849,194 (now issued as U.S. Pat. No. 6,615,824), filed May 4, 2001, which claims the benefit of Ireland patent application Ser. No. PCT/IE/00051, filed May 5, 2000, which are incorporated herein in their entirety; and 2) a continuation-in-part of U.S. patent application Ser. No. 09/8 12,755 (now issued as U.S. Pat. No. 7,100,600), filed Mar. 20, 2001, which is incorporated herein in its entirety; and 3) a continuation-in-part and claims the benefit of U.S. Provisional Application No. 60/349,763, filed Jan. 15, 2002, which is incorporated herein in its entirety; and 4) a continuation-in-part and claims the benefit of U.S. Provisional Application No. 60/349,805, filed Jan. 15, 2002; 60/380,655, filed May 14, 2002; 60/408,743, filed Sep. 5, 2002; and 60/439,045, filed Jan. 8, 2003, entitled "Methods and Systems for Operating an Aerosol Generator", which are incorporated herein in their entirety; and 5) a continuation-in-part of U.S. patent application Ser. No. 10/284,068, filed Oct. 30, 2002, which claims the benefit of U.S. Provisional Application No. 60/344,484, filed Nov. 1, 2001 and 60/38 1,830, filed May 20, 2002, entitled "Apparatus and methods for delivery of medicaments to a respiratory system", which are incorporated herein in their entirety; and 6) a continuation-in-part of U.S. patent application Ser. No. 09/876,542, filed Jun. 7, 2001, now abandoned Ser. No. 09/876,402, filed Jun. 7, 2001, now abandoned and Ser. No. 09/812,987 (now issued as U.S. Pat. No 6,948,491), filed Mar. 20, 2001, the complete disclosures of which are incorporated herein by reference.

BACKGROUND OF THE INVENTION

The present invention is generally related to liquid aerosol generators. In particular, the present invention is related to methods and devices for identifying the contents of a nebule to improve the delivery of the aerosolized liquid to the patient.

The ability to aerosolize or nebulize small liquid droplets is important in a variety of industries. Merely by way of example, many pharmaceuticals can now be delivered to the lungs in liquid droplet form through use of an aerosol generator, such as a nebulizer inhaler. Aerosolization is also a useful technique to dispense deodorizers, perfumes, insecticides, or the like, into the atmosphere or to other target areas.

Aerosol generators can be configured to deliver a number of different pharmaceutical aerosols to the patient's lungs or other target areas of the body. Typically, the aerosol generator will utilize a removable supply of a liquid pharmaceutical that is contained in some type of portable nebule, such as an ampoule, container, canister, reservoir, or the like.

While the existing aerosol generators have proven to be effective, the existing aerosol generators suffer some limitations. One problem with existing aerosol generators is that users may inadvertently install and nebulize an incorrect drug nebule into the aerosol generator. As can be appreciated, delivery of the wrong drug can be extremely dangerous, if not fatal.

Another problem with existing aerosol generators is that the aerosol generator cannot identify the liquid in the nebule. Consequently, it has proven to be difficult to provide an efficient delivery of the aerosolized pharmaceutical to the patient. Since some of the pharmaceuticals to be aerosolized may be more effective when delivered near the beginning of a patient's breathing cycle, while other pharmaceuticals may be more effective when delivered near the end of the patient's breathing cycle it is preferable that the aerosol generator be able to identify the type of liquid disposed in the nebule so that the correct delivery sequence can be chosen to deliver the aerosol to the patient. While the existing nebulizers have proven to be effective within certain parameters, the existing nebulizers also present opportunities for improvements.

One area for improvement is the calculation and control of the precise time of aerosol delivery within a user's or patients breathing cycle. This is especially in issue with respect to patients that receive some of all of their inspiratory air from a ventilator device. Existing nebulizers may deliver a constant flow of aerosol into the ventilator tubing, which can lead to a significant amount of aerosol lingering in the tubing or other elements of the overall ventilator system—this lingering aerosol may not be inhaled, as it collects while the patient is exhaling or otherwise not inhaling, resulting in a significant amount of aerosolized medication being pushed out of the system, such as during exhalation, without being inhaled by the patient. Such situations are problematic for a number or reasons. First, the dosage of drug that actually is inhaled by the patient may be significantly inaccurate because the amount of medication the patient actually receives into the patient's respiratory system may vary with fluctuations of the patient's breathing pattern. Further, a significant amount of drug that is aerosolized may end up being wasted, and certain medications are quite costly, thus health-care costs can be escalated. Further still, unused aerosolized medication will typically be released to the ambient atmosphere with a patent's exhalation. This can end up medicating individuals in the patient's surroundings and this may give rise to adverse effects with respect to such individuals. Moreover, in a hospital environment such individuals may be either health-care providers, who could be exposed to such air pollution over a prolonged period of time, or other patients, who may be in a weakened condition or otherwise overly sensitive to exposure to non-prescribed or excessive amounts of a medication.

For these reasons, it is desired to provide an aerosol generator that can obtain information about the contents of the nebule. In particular, it is desired to provide methods and devices, which can determine the type of liquid disposed in the drug so as to provide an improved level of safety to the patient and an increased efficiency in the delivery of the aerosol to the patient. Further, for these reasons, it is desired to provide methods and devices that can provide aerosol to a patient at a selected interval of the breathing cycle. It is also desired to provide methods and devices that can provide aerosol to a patient at a selected interval wherein the interval is selected based on the identity of the drug to be administered.

BRIEF SUMMARY OF THE INVENTION

The present invention provides devices and methods for improving a level of safety to the patient and for providing an increased efficiency of delivery of an aerosol to the patient.

In one method, the present invention provides a method of creating an aerosol. The method comprises providing an aerosol generator and coupling a nebule to an interface of the aerosol generator. An identification marker is read on the nebule and the aerosol generator is operated according to an operation program based on the information read from the identification marker on the nebule.

In another method, the present invention provides a method of nebulizing a liquid. The method comprises taking one or more breaths and measuring characteristics of the breath. Another breath is taken and an aerosol generator is operated based on the measured characteristics of the one or more measured breaths.

In yet another method, the present invention provides a method comprising providing a nebulizer system comprising a housing, an aerosol generator, a controller coupled to the aerosol generator, and a reservoir in communication with the aerosol generator. A nebule having a body and a keying element is provided. The nebule is inserted into the housing so that the key element provides access to the reservoir when properly keyed with the housing. The liquid is transferred from the nebule into the reservoir and the aerosol generator is operated with the controller to aerosolize the liquid.

In another aspect, the present invention provides an aerosol generator comprising an interface. A sensing device is coupled to the aerosol generator. An ampoule having at least one identification marker that can detected by the sensing device is attachable to the interface.

In another aspect, the present invention provides a nebulizer system comprising a housing that defines a passageway that is adapted to deliver an aerosolized liquid to a user. An aerosol generator is positioned to provide an aerosolized liquid into the passageway. A controller having a memory and a plurality of aerosol generator operation programs that control operation of the aerosol generator is coupled to the aerosol generator. A reader is configured to read an identification marker on a nebule having a supply of liquid for the aerosol generator, and is configured to send information from the identification marker to the controller. Typically, the controller is further configured to operate the aerosol generator according to one of the operation programs based on the information from the marker.

In another aspect, the present invention provides a nebule comprising a nebule body holding a liquid that is adapted to be supplied to an aerosol generator of a nebulizer; and an identification marker on the nebule body, the identification marker having information identifying the liquid, wherein the identification marker is readable by a nebulizer to control operation of the aerosol generator based on the information.

In another aspect, the present invention provides a nebulizing element positioned to provide nebulized fluid into a ventilator breathing circuit to provide nebulized fluid to a patient receiving air from a ventilator. It will be appreciated that a nebulizing element may also be referred to herein a an aerosolization element, and a ventilator may also be referred to herein as a respirator.

In another aspect, the present invention provides operation sequences by which aerosol is provided a predetermined points in a breath cycle provided by a ventilator. In one aspect, the present invention provides for an operation sequence in which aerosol production begins at a predetermined point within an inhalation phase, which may also be referred to herein as an inspiratory phase, and stops at a second predetermined point within the same inhalation phase. In another aspect, the present invention provides for an operation sequence, which may be referred to as an operation program, in which aerosol production begins at a predetermined point in an inhalation phase and stops at a point after the inhalation phase has ended, i.e. at a certain point in the exhalation phase. It will be appreciated that the exhalation phase may also be referred to as the expiratory phase, and may encompass the entire period of time during which no inhalation phase is taking place; in other words, the exhalation phase may include not only the actual exhalation of the patient, but also any pause that may occur before or after exhalation. In another aspect, the present invention provides an operation sequence in which aerosolization begins at a predetermined point within the exhalation phase and stops within that exhalation phase, or, alternatively, begins at a predetermined point within an exhalation phase and stops at a predetermined point in the succeeding inhalation phase.

In another aspect, the present invention provides for selection of a particular operating sequence from a plurality of available operating sequences. Similarly, the present invention provides for modes of operation, which modes may include one or more operating sequences.

In another aspect, the present invention provides for algorithms to set forth operation sequences, choice of operation sequences or choice of modes of operation.

In another aspect, the present invention provides for consideration of the identity of a drug to be administered in executing an algorithm, choosing a mode of operation, or selecting or running an operation sequence.

In another aspect, the present invention provides for nebulization of particular drug groups or drugs, such as, for example, antibodies, such as IgG or antibiotics, such as aminoglycosides, such as amikacin.

In another aspect, the present invention provides for a nebulized droplet ejection device for use with a ventilator, wherein the device produces droplets by a vibratory apertured element during a selected interval of a breathing cycle.

In another aspect, the present invention provides for apparatus and methods for varying the particle size distribution of a nebulized mist by varying the aperture exit diameter of an apertured vibratory aerosolization element.

For a further understanding of the nature and advantages of the invention, reference should be made to the following description taken in conjunction with the accompanying drawings.

BRIEF DESCRIPTION OF THE DRAWINGS

FIG. 1 schematically shows a system of the present invention;

FIG. 11 illustrates a simplified flowchart illustrating one exemplary method of the present invention;

FIG. 12 illustrates another simplified method of the present invention;

FIG. 13 illustrates yet another simplified method of the present invention; and

FIG. 14 illustrates another simplified method of the present invention.

FIG. 15 is a graph showing various modes of aerosolization over the course of breathing cycles;

FIG. 16b is a schematic cutaway cross-section detail of the aerosol generator represented in FIG. 16a.

FIG. 18 is a schematic representation of algorithms of operating sequences in accordance with the present invention;

FIG. 19 s an alternative schematic representation of the representation of FIG. 18;

FIG. 20 is a further schematic representation of algorithms of operating sequences shown in FIG. 19 and in accordance with the present invention.

DETAILED DESCRIPTION OF THE INVENTION

Figure 2:
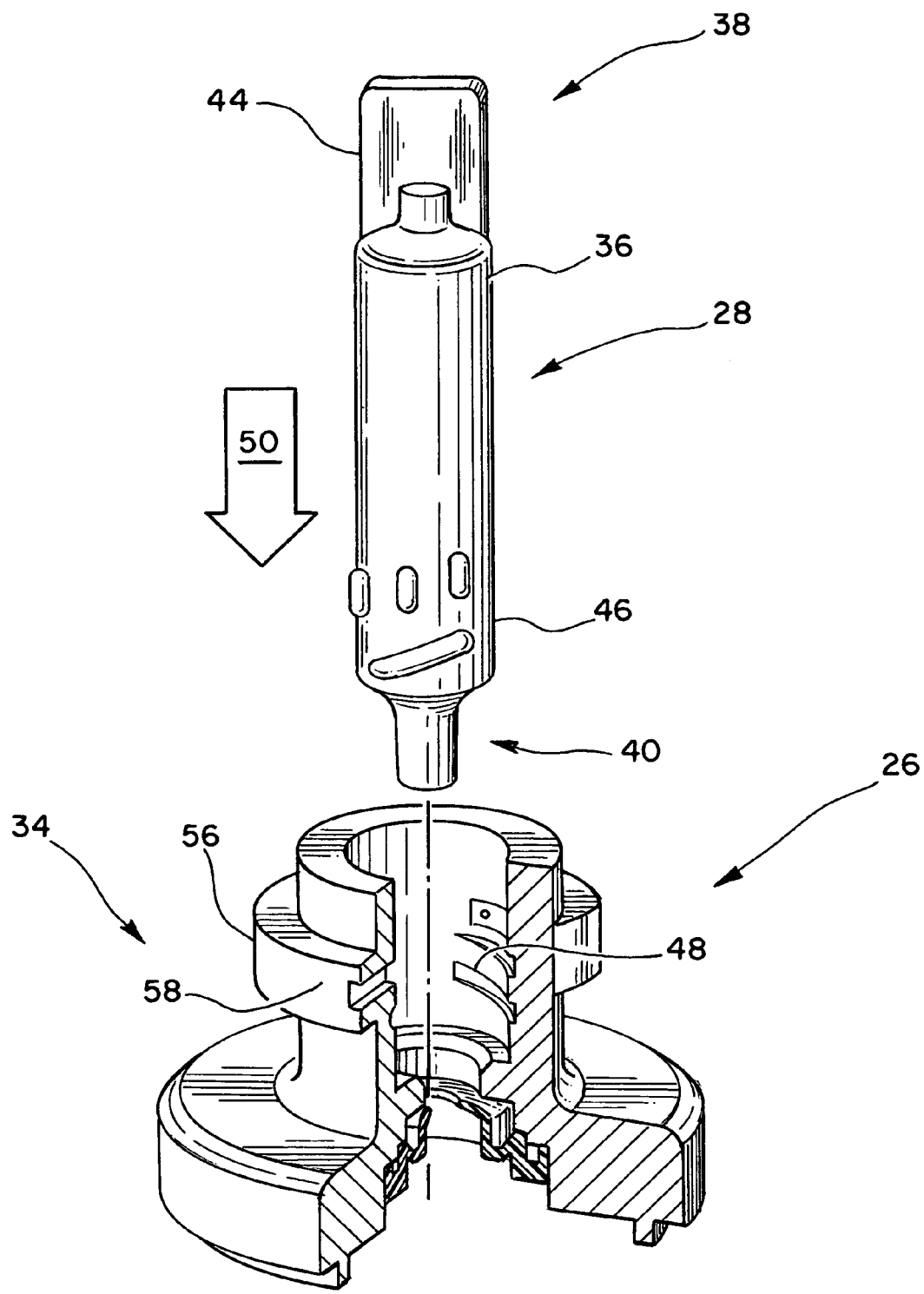
FIGS. 2 to 4 illustrate an exemplary nebule and feed system interface of the resent invention.

The aerosol generator systems of the present invention, in one aspect, include an aerosol generator coupled to a controller that is in communication with at least one sensor such that delivery sequence of the aerosol to the patient can be based at least in part on the information obtained with the sensors. In some exemplary embodiments, the system includes a nebule identification sensor to read an identification marker on the nebule so as to identify the type of liquid that is disposed within the nebule. In other exemplary embodiments, the system includes a breathing characteristic sensor that monitors and records the breathing characteristics of the patient so as to allow the controller to direct the delivery of the aerosol to coincide with the patient's breathing pattern. In yet other exemplary embodiments, the aerosol generator system includes both a nebule identification sensor and a breathing characteristic sensor.

Figure 1:
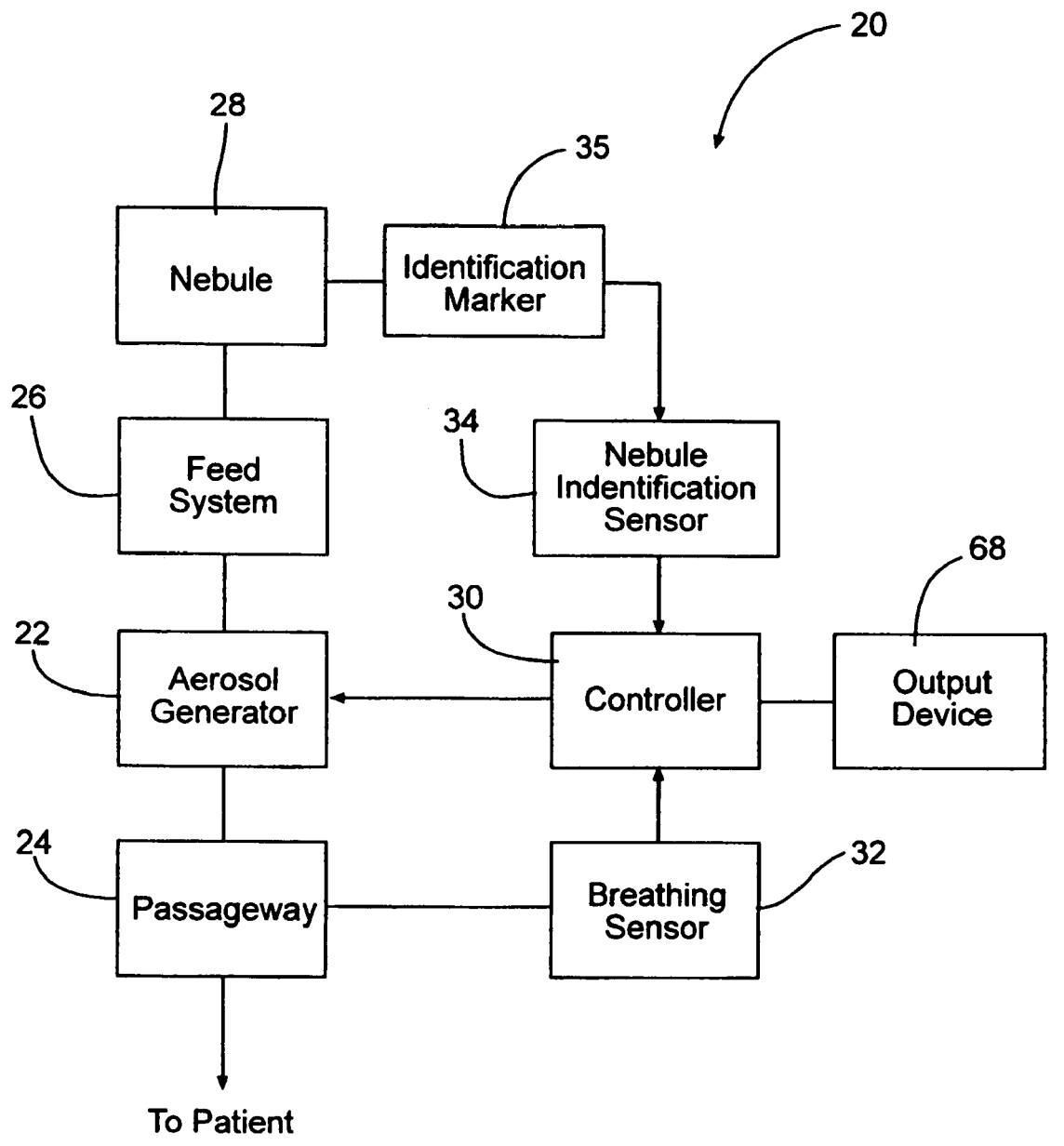

FIG. 1 schematically illustrates an exemplary aerosol generating system 20 of the present invention. The system 20 includes an aerosol generator (AG) 22 that is in communication with an output passageway 24, such as a ventilator circuit, mouthpiece, face mask, or the like. A nebule 28 containing a liquid can be removably coupled to a feed system interface 26 to deliver a liquid to aerosol generator 22 for aerosolization. A controller 30 is in communication with aerosol generator 22 to control the sequence of aerosolization of the liquid to the patient. Controller 30 can be coupled to a breathing sensor 32 that is in communication with output passageway 24 so as to monitor the breathing characteristics of the patient. Additionally or alternatively, controller 30 can be coupled to nebule identification sensor 34 to identify the type of liquid that is disposed in nebule 28 by reading an identification marker that is provided on nebule 28. Controller 30 can take the information from flow sensor 32 and/or nebule sensor 34 and run the information through an algorithm to determine an efficient sequence of aerosolization. Typically, the controller will run a selected pre-programmed delivery or sequence program that is stored in controller 30 so as to deliver the aerosol to the patient in an optimal time of the patient's breathing cycle.

Controller 30 can include a memory and a microprocessor so as to store and run the algorithm that selects the pre-programmed drug delivery sequence. The memory of the controller can store a list or library of codes and/or drugs that are compatible with the aerosol generator, information about the drugs, such as a regime to be followed based on the particular drug, the time in the breathing cycle when the drug is best administered, the amount of the drug to be aerosolized, or the like.

Controller 30 will typically be in communication with at least one sensor. As noted above, one sensor can be a nebule identification sensor 34 that reads an identification marker on the nebule to identify the type of liquid disposed within the nebule. The sensor can be a mechanical sensor, an electromechanical sensor, an electrical sensor, an optical sensor or the like. Such sensors can be used to provide information to the controller for a number of purposes. For example, the identification information can be used to identify the type of drug so as to choose the delivery sequence program. Moreover, the identification information can be used as a quality control mechanism to prevent the aerosolization of an incompatible, unsafe, or unknown drug, and the like.

Another type of sensor that can be coupled to controller 30 is a breathing characteristic sensor 32 that can monitor the breathing characteristics of the user. The sensor can send breathing characteristic information to the controller to allow the controller to select an appropriate delivery cycle of the aerosolized liquid to the patient. Typically, breathing characteristic sensor 32 can be used to measure a breathing pattern of the patient, the peak flow, breathing rate, exhalation parameters, regularity of breathing, and the like. Such measured breathing characteristics can be delivered to controller 30 and run through a software algorithm to determine an appropriate sequence of delivery relative to the measured breathing cycle to the patient. One exemplary breathing characteristic that may be sensed by sensor 32 is the cycle of a ventilator providing air to a patient; for example, the start of an inhalation cycle generated by the ventilator. The sensor 32 may sense other parameters, for example, it may be an acoustic sensor that is activated through passing the respiratory flow of the patient through an acoustic chamber (not shown) so as to produce an acoustic tone, which is proportional to the inspiratory flow rate. The frequency of the acoustic tone indicates the inspiratory flow rate at any instant of the breathing cycle. The acoustic signal can be detected by the controller such that integration of the flow rate with time produces the tidal volume. Both the flow rate and the tidal volume can then be used by the controller to determine when the aerosol generator generates the droplets and at what mass flow rate such that maximum deposition of droplets is obtained. Further, the acoustic tone may be recorded to produce a record of the breathing pattern of the patient which may be stored in the microprocessor. This information can be later used to synchronize the ejection of droplets for the same patient. Such information may also be later employed for other diagnostic purposes. A more complete description of such a sensor is described in commonly owned, U.S. Pat. No. 5,758,637, which was previously incorporated by reference.

In some embodiments, the sensor can be used to monitor the breathing characteristics of the patient throughout the delivery regime so as to ensure that the aerosol is efficiently delivered throughout the aerosolization procedure. In such embodiments, the controller can adjust the aerosol delivery based on any measured change in the breathing pattern of the patient during the aerosolization. With this monitoring and adjustment predetermined times for the beginning and ending of aerosolization can be reset based on the actual breathing of the patent. In other embodiments, however, the breathing sensor can be used to determine the breathing cycle of a tidal breath and to choose the appropriate pre-programmed delivery cycle that is stored in the memory of the controller. In other embodiments, the controller may be configured to provide aerosol based on the time. For example, the controller may be configured to start aerosol production at the beginning of an inhalation phase of a breathing cycle and stop at a point at which a predetermined percentage of the inhalation has taken place. Alternatively, the controller may be configured to start aerosolization at a first point at which a first predetermined percentage has taken place and stop aerosolization at a second point at which a second predetermined percentage of that inhalation has taken place. Alternatively, aerosol may begin during an inhalation phase and end during the subsequent exhalation phase. Alternatively, the controller may be configured to begin aerosol production at a certain point during exhalation and stop during that exhalation or during the subsequent inhalation. Thus, an aspect of the present invention may include a nebulizer comprising: an aerosol generator and a controller configured to have the controller begin aerosolization during exhalation and stop during that exhalation or in the subsequent inhalation. In addition, the controller may be operable to allow for a choice of modes of operation, for example, a mode in which aerosolization begins once a certain breath characteristic is detected, such as a sufficient level of inhalation, and ends when there is no longer a sufficient level; another mode in which aerosolization begins once a certain breath characteristic is detected, such as a sufficient level of inhalation, and ends at a predetermined time within the inhalation cycle, such as for example, before the level of inhalation falls below that required for operation of an aerosolization element, or, alternatively, at any other point within the inhalation cycle, such as after the inhalation phase of the cycle before exhalation has begun, or after exhalation has begun.

The level of inhalation may be sensed by a pressure transducer. Such a transducer may monitor a drop in air pressure or a rise in air pressure within a chamber that is in fluid communication with the ventilator circuit. In this manner, a pressure drop may be sensed by a patient inhaling through the circuit, for example, in an instance in which the ventilator provides an assisted ventilation initiated by a patient's commencement of an inhalation. Similarly, a pressure rise may be sensed in an instance in which the ventilator pushes inhalation air to the patient without the patient initiating a breath. Another mode in which the controller may be operable is a mode in which the on/off operation of the aerosol generator is triggered by time, which may be ascertained from an internal clock device, such as a clock built into a microprocessor, or from an external source. Another mode in which the controller may be operable is in which the on/off operation of the aerosol is triggered by the controller receiving an external signal, such as a signal from a ventilator, which can correspond to the point in the ventilator's cycle of that is the start of an inhalation phase in which the ventilator begins to push inspiratory air into the ventilator circuit. The controller may be operable between such modes, including a mode in which the aerosolization begins at a predetermined time in the breathing cycle and ends at a predetermined time in the breathing cycle. The first and second predetermined times in the third mode may be during inhalation. Alternatively, the first and second predetermined times may be during exhalation, or at the first predetermined time may be during exhalation and the second predetermined time may be during subsequent inhalation. These times may correspond to certain percentages of the inhalation phase taking place, or any other points of reference within a breathing cycle.

Alternatively, the first predetermined time and the second predetermined time may be designated as any point within a single breathing cycle, or alternatively, the first predetermined point may be at any point within one breathing cycle and the second predetermined point may be at any point in a subsequent breathing cycle. The controller may make the determination of when to begin, and operate to begin aerosolization, and may make the determination of when to stop aerosolization to stop, and cause aerosolization to stop. The controller may make such determinations and take such actions based on accessing stored algorithms. The controller may receive a signal from the ventilator that establishes a reference point, nonetheless, the controller, by making the determinations an taking the actions based on stored algorithms, and/or information obtained as to the identity of a drug to be administered, may cause aerosol production to begin and/or end independent of the instantaneous position of the ventilator with respect to the ventilator cycle.

The controller may be operable to allow for a single mode of operation, and such single mode of operation may be any mode, for example, as described above. For example, a mode in which aerosolization begins once a certain breath characteristic is detected, such as a sufficient level of inhalation, and ends when there is no longer a sufficient level. Similarly, the controller may operable in a mode in which aerosolization begins once a certain breath characteristic is detected, such as a sufficient level of inhalation, and ends at a predetermined time within the inhalation before there is no longer a sufficient level or an aerosolization element.

Alternatively, the mode may be a mode in which the aerosolization is commenced based on a signal from the ventilator indicating the attainment of a certain point within the ventilation output cycle or the inhalation cycle of the patient. (The ventilation output cycle of the ventilator may coincide with the inhalation cycle of the patient, such that the ventilation output phase of the ventilator output cycle and the inhalation phase of the inspiratory cycle of the patient occur substantially simultaneously. Such may be the case where a patient is completely passive and the only inhalation that occurs is by generation of air from the ventilator during the output phase of the ventilator cycle.). Such point may be during the output phase of the output cycle of the ventilator or during the inhalation phase of the inhalation cycle of the patient. The predetermined point can be chosen to coincide with a certain level of output from the ventilator or at a certain point in time during the ventilator output cycle. Such a predetermined point may be a specific point within the output phase of the ventilator cycle, or, a specific point within the non-output phase of the ventilator cycle, based, for example, on the timing of the previous or succeeding output phase of the ventilator. In another aspect, the present invention provides for a ventilator along with the aerosol generator and controller. In an aspect of the invention, a predetermined time may be based on the timing of a ventilator supplying air to a user. In this manner, the controller may be set to work off of the timing of the ventilator in one mode, while working off the patient's inspiratory effort in another mode, or mode that allows for a combination of the patient's inspiratory effort and the timing of the ventilator, for example, where the ventilator is set to assist the patient by supplying air upon the patient's effort or where the patient has not made a sufficient effort within a predetermined period of time.

In regard to the aerosol generators 22 of the present invention, they may be of the type, for example, where a vibratable member is vibrated at ultrasonic frequencies to produce liquid droplets. Some specific, non-limiting examples of technologies for producing fine liquid droplets is by supplying liquid to an aperture plate having a plurality of tapered apertures and vibrating the aperture plate to eject liquid droplets through the apertures. Such techniques are described generally in U.S. Pat. No. 5,164,740; 5,938,117; 5,586,550; 5,758,637, 6,014,970, and 6,085,740, the complete disclosures of which are incorporated by reference. However, it should be appreciated that the present invention is not limited for use only with such devices.

FIGS. 2 to 10 illustrate some exemplary feed system interfaces 26 and nebules 28 of the present invention. As shown in FIG. 2, nebule 28 can be an ampoule that comprises a body 36 with a top end 38 and a bottom end 40. Bottom end 40 can include a tapered opening that can deliver the liquid from ampoule 28 into a fluid reservoir 42 adjacent aerosol generator 22. Top end 38 can include a twist-off vent 44 that can be removed to create a drain vent in top end 38. Some exemplary ampoules that can be used with the present invention are described in co-pending U.S. patent application Ser. No. 09/812,755, filed Mar. 20, 2001, the complete disclosure of which was previously incorporated by reference.

The ampoules of the invention may be used to store a wide variety of liquids. Merely by way of example, liquids that may be stored within the ampoules include various pharmaceuticals such as saline, albuterol, chromatin, budesinide, nicotine, THC, cocaine, antibodies, such as IgG, antibodies, such as aminoglycosides, and the like. Other liquids that may be stored include insecticides, deodorizers, perfumes, and the like. Hence, it will be appreciated that the ampoules of the invention may be used to store essentially any type of liquid that is capable of being aerosolized.

The ampoules of the invention may be constructed by blowing or vacuum-forming the ampoule in a mold, filling the ampoule with liquid, and melt-sealing the liquid into the ampoule. The ampoules may further be provided with a set of removable tabs to provide a drain vent and a drain opening. Typically, these will be located in the top and bottom of the ampoule so that the liquid may drain by force of gravity once the openings are formed. The tabs may be removed by twisting, cracking, or the like so that the opening may be formed. In some cases, the ampoules may be configured to be opened simply by piercing the top and/or bottom end. Such piercing elements may conveniently be incorporated into the aerosolization device.

Various materials may be used to construct the ampoules, such as moderate durometer polymer materials, thermoplastic synthetics, such as low density polyethylene and polypropylene, and the like. The ampoules may be provided with a thick enough wall to minimize droplet spillage. For instance, the wall thickness may be greater than about 0.030 inch. The ampoule may further be configured so that the diameter of the drain opening minimizes the drip potential for the fluid stored within the ampoule. For example, larger diameter openings may be provided when storing higher viscosity fluids and smaller diameter openings may be used for low viscosity fluids.

Figure 3:
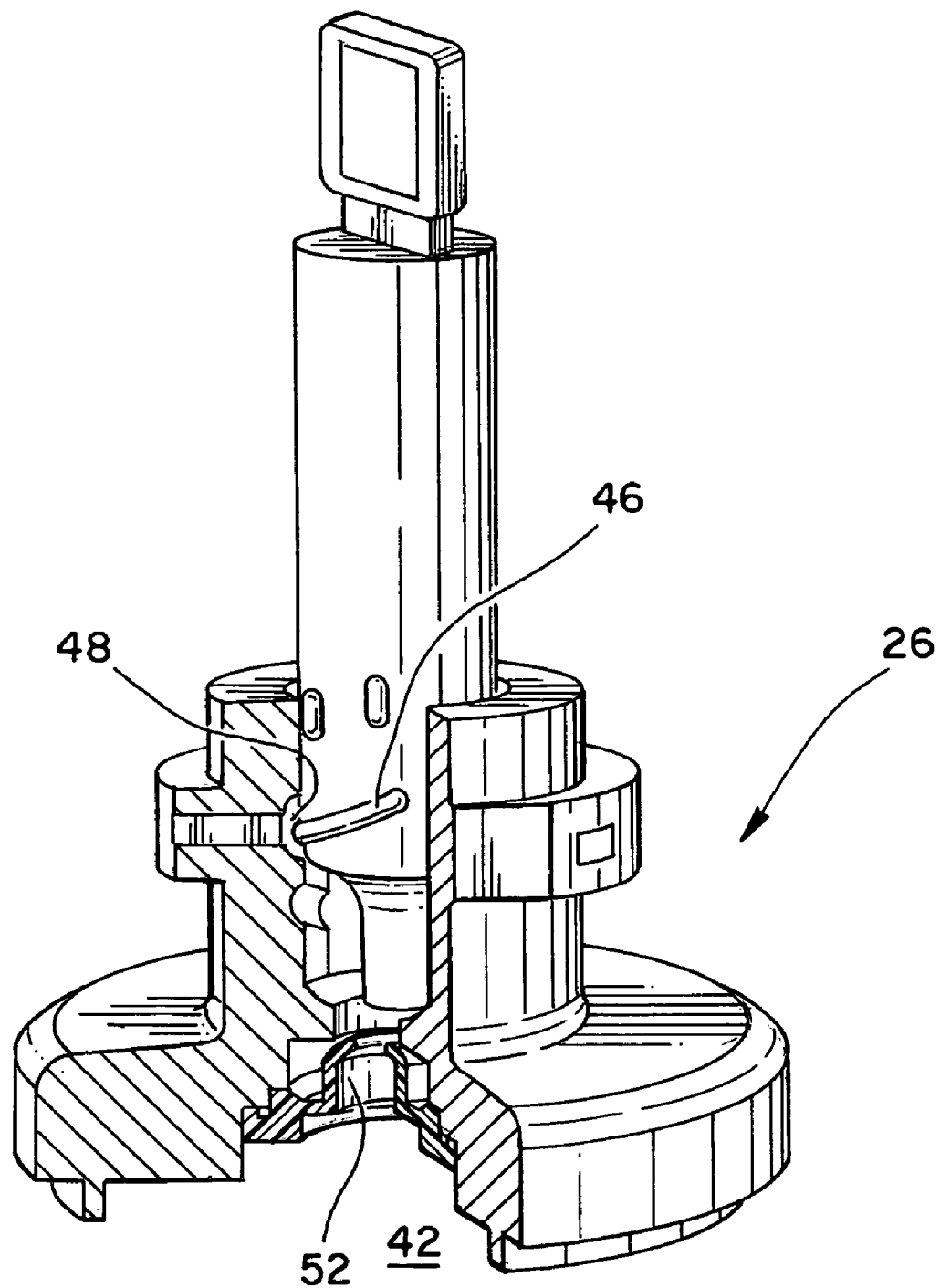
Figure 4:
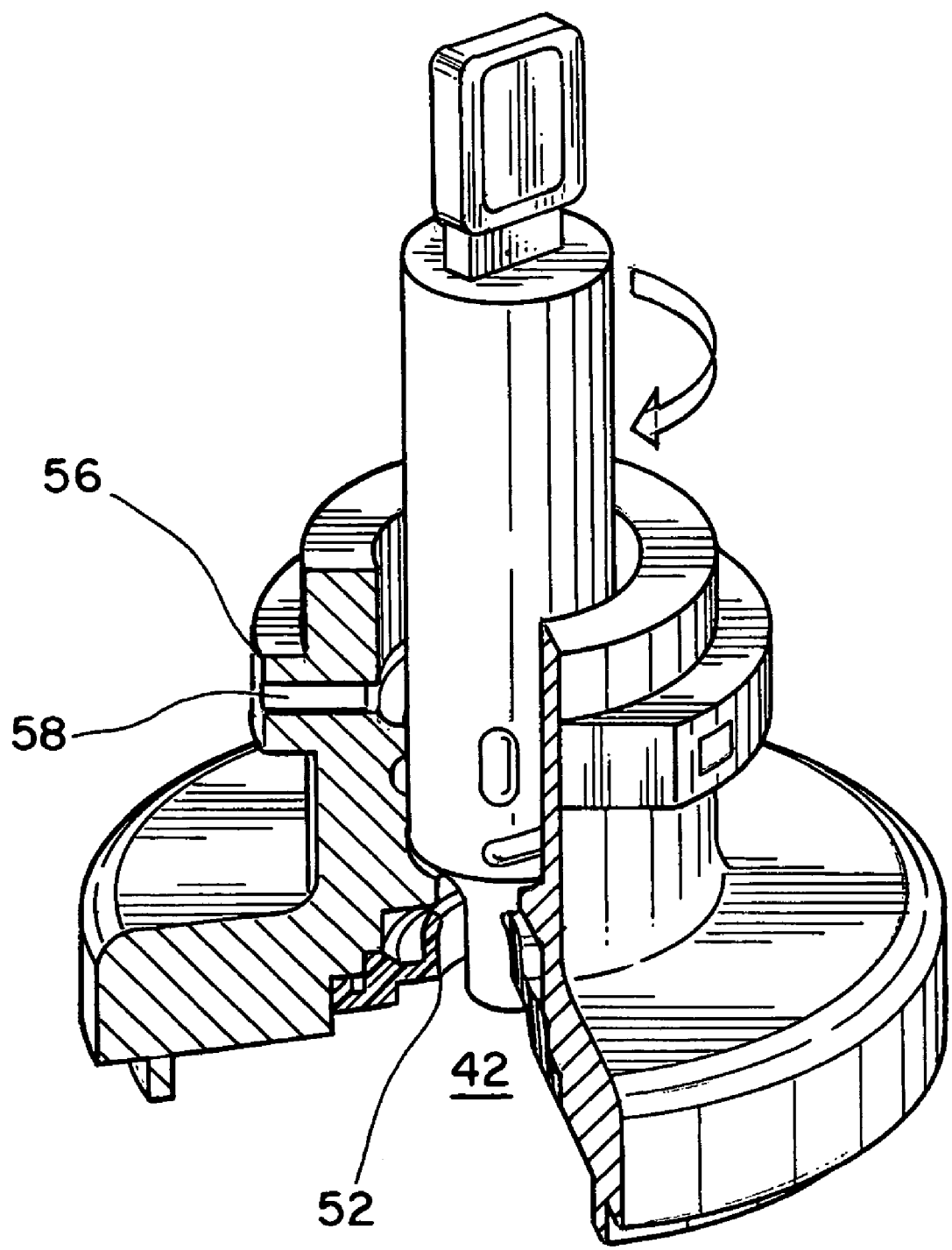

The ampoules of the present invention can include a connection or keying element 46, such as a thread or a tab so as to accurately align the ampoule 28 with a nebulizer feed system interface 26. The feed system interface 26 will have a corresponding feature or slot 48 to engage the connection element. In the exemplary embodiment illustrated in FIGS. 2 to 4, ampoule 28 can include a helical keying element 46 that is shaped to mate With the corresponding keying feature 48 in feed system 26. To insert the ampoule into feed the system, the ampoule is moved axially (in the direction of arrow 50) until helical keying element 46 is positioned adjacent the corresponding keying feature 48. Thereafter, the ampoule 28 is rotated to mate the keying element 46 and the keying feature 48 together so as to pull the ampoule 28 axially downward until the bottom end 40 of the ampoule 28 opens slit seal membrane 52 in feed system 26 (FIGS. 3 and 4).

In the exemplary embodiments, ampoule 28 includes an identification marker 35 to identify to the controller, the liquid that is within ampoule 28. Identification marker 35 can be a bar code (e.g., embossed or printed), one or more bumps or protrusions, a radio frequency identifier, a small chip containing stored information, or other suitable identification technology. In the embodiments depicted in FIGS. 2 to 4, information regarding the contents of the ampoule is conveyed through a series of protrusion identification markers 35 on the ampoule 28 that are sensed by their interaction with an optical detector 56 during the rotational engagement of ampoule 28 with the feed system interface 26. In this particular embodiment, a miniature light source 58 and the optical sensor 56 are coupled to the feed system 26 such that a passing protrusion 35 affects the sensed light in a manner such that the sensor 56 may provide information (e.g., typically binary information, i.e., a "0" or a "1") based on position, number, or absence of the protrusion.

Thus, rotation of an ampoule 28 as it is threadedly inserted into the nebulizer feed system 26 may count the number of bumps or provide a code such as "1-0-1-0" so as to inform the nebulizer controller 30 (FIG. 1) the type of medicant or other liquid that is disposed in the ampoule. A single sensor can read the code imparted by a series of protrusions as the ampoule 28 is moved axially into the nebulizer feed system 26 while it is rotated through the threaded features in the housing of feed system 26.

Figure 5:
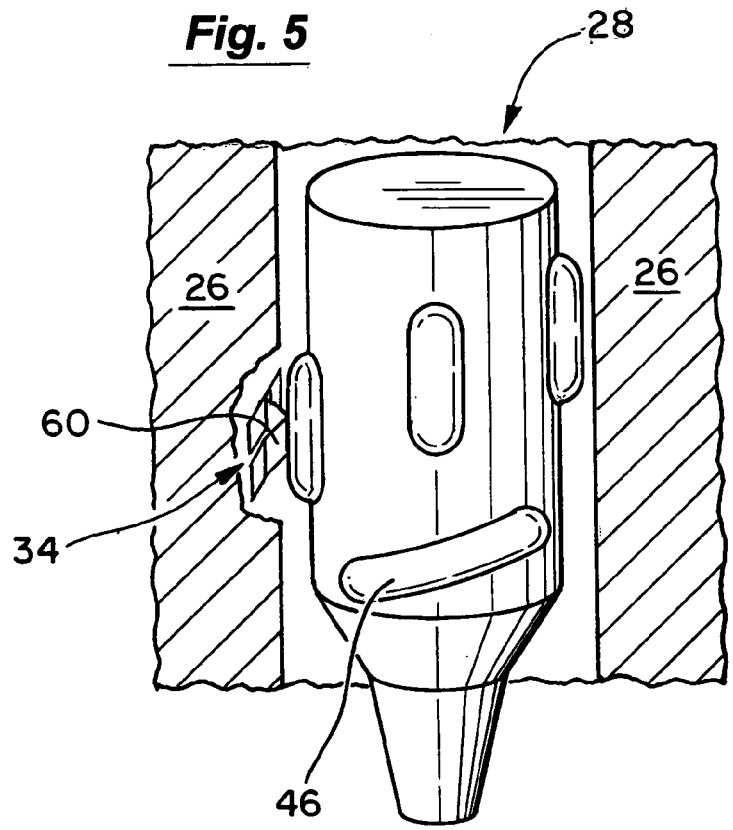
FIG. 5 shows an elevational view of another exemplary system of the present invention comprising an electromechanical sensor.
Figure 6:
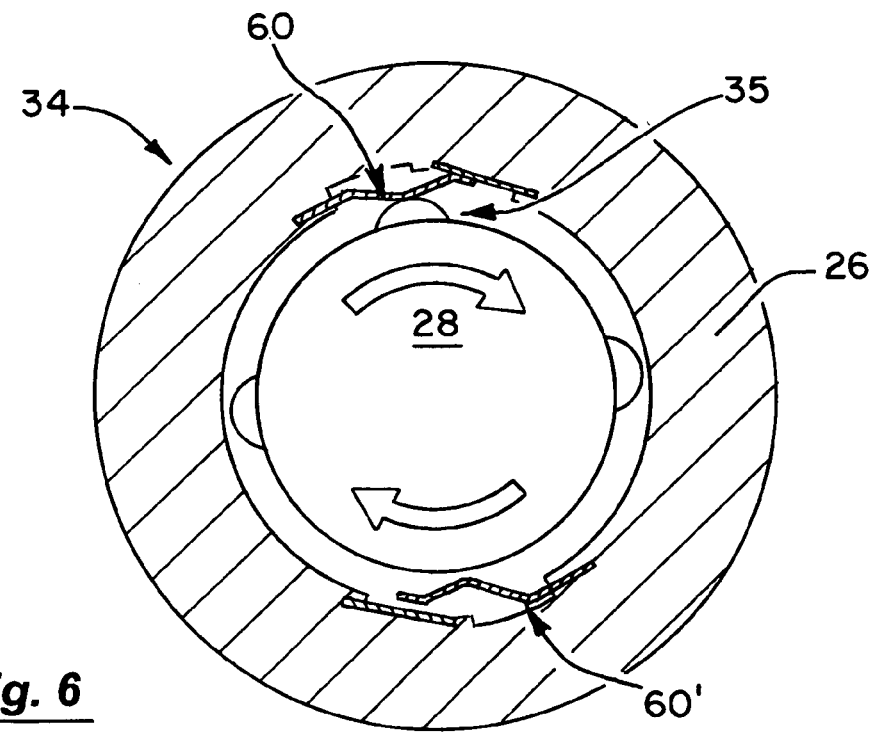
FIG. 6 shows a plan view of an ampoule and an electromechanical sensor of FIG. 5.

FIG. 5 illustrates another exemplary nebule identification sensor 34 and ampoule 28. Nebule sensor 34 can include an electromechanical switch that contacts the protrusions on the nebule as it is inserted into the feed system. As shown in FIG. 5, the nebule includes a helical keying element 46 that interacts with a corresponding helical keying feature (not shown) to position the ampoule within feed system interface 26. As the ampoule is rotated and moved axially downward, the protrusion identification markers will contact and actuate a metal spring-like contact 60 of nebule sensor 34 so as to create a circuit and send an identification electrical signal to controller 30 to identify the type of drug in ampoule 28. As shown in the plan view of FIG. 6, nebule sensor 34 can include one or more metal contacts 60, such that rotation of the ampoule 28 can cause the protrusion identification markers to contact the metal contacts 60, 60'. By changing the spacing and number of protrusion identification markers, a unique electrical identification signal can be generated to identify the liquid in the ampoule to the controller. In turn, the controller can then select and run a delivery program that provides an efficient delivery of the identified liquid.

Figure 7:
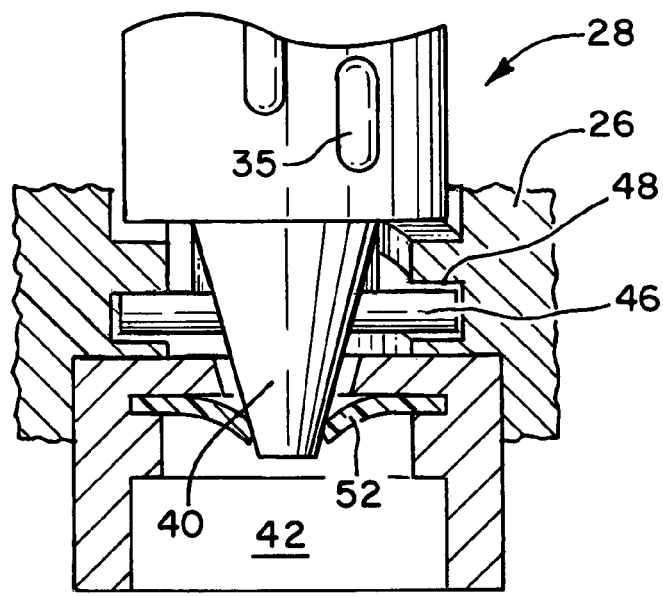
FIGS. 7 and 8 show an ampoule and feed system interface having an alternative threaded interface.
Figure 8:
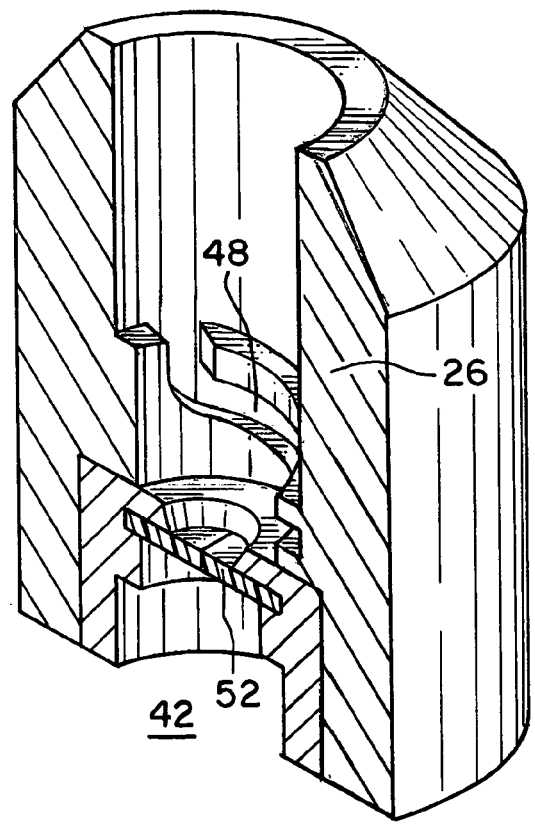

Another exemplary ampoule 28 and feed system interface 26 is illustrated in FIGS. 7 and 8. As shown in FIG. 7, an ampoule bottom end 40 having a keying tab 46 can interact with a spiral slot 48 in the feed system interface 26. As the ampoule is inserted and rotated within the feed system interface 26, the keying element(s) engage the spiral slot 48 so as to pull the ampoule down into the interface (FIG. 8). Similar to the above embodiments, the bottom end of the ampoule can protrude through slit seal membrane 52 so as to be able to deliver the liquid to reservoir 42. Identification markers 35 can be sensed by the identification sensors (not shown), as described in the above embodiments.

The ampoule protrusion identification markers 35 can be in a single helix configuration or a double helix configuration. In exemplary embodiments, the identification markers are in a double helix arrangement so that as the first set of protrusions is read, providing a binary code to the system, the second set of protrusions can provide a complementary binary code (read by a second optical detector, not shown) as ampoule 28 is screwed into nebulizer feed system 26 (FIGS. 2 to 4). Thus, the binary code of the first series of protrusions might, for example, convey the code "1-0-1-0" as each of protrusions are sensed as the ampoule is screwed into the nebulizer feed system housing, while the second series provides the complementary code of "0-1-0-1". In this manner, the controller can check that when a particular binary code is transmitted by the first set of protrusions, the complementary binary code is sensed by the second set of protrusions. Thus, the system can prevent the potential mis-information that might be transmitted were there only a single set of protrusions provided to convey the information, and the insertion was done incorrectly.

Such interaction further allows the system to check against a situation in which one or more ampoule protrusions are damaged to the extent of effecting the sensing function, because the system will have the code provided by the second series of protrusions to check against the information provided by the first set of protrusions.

Alternatively, the second set of protrusions may be used to provide more code combinations for different drugs. In exemplary embodiments, by providing three bumps or protrusions on each side of the ampoule, the controller of the aerosol generator can determine which of 9 drugs or medicants are disposed in the ampoule. For example, the following distribution of bumps or protrusion can deliver a signal to the controller to indicate the identity of the following drugs:

| Drug Type | Number of Bumps on Side 1 | Number of Bumps on Side 2 |
| --- | --- | --- |
| Drug A | 1 | 0 |
| Drug B | 2 | 0 |
| Drug C | 3 | 0 |
| Drug D | 1 | 1 |
| Drug E | 2 | 1 |
| Drug F | 3 | 1 |
| Drug G | 2 | 2 |
| Drug H | 2 | 3 |
| Drug I | 3 | 3 |

In the embodiment illustrated in FIGS. 2 to 8, the protrusion identification markers 35 are disposed in a helical configuration that has a pitch that substantially matches the pitch of the helical keying element 46, such that as the helical keying element is rotated and moved through the corresponding keying feature 48, the protrusion identification markers pass by the optical sensor 56 or metal contacts 60. It should be appreciated however, that the identification markers 35 can be disposed in a variety of non-helical patterns, as will be described in relation to FIGS. 9 to 10.

Figure 9:
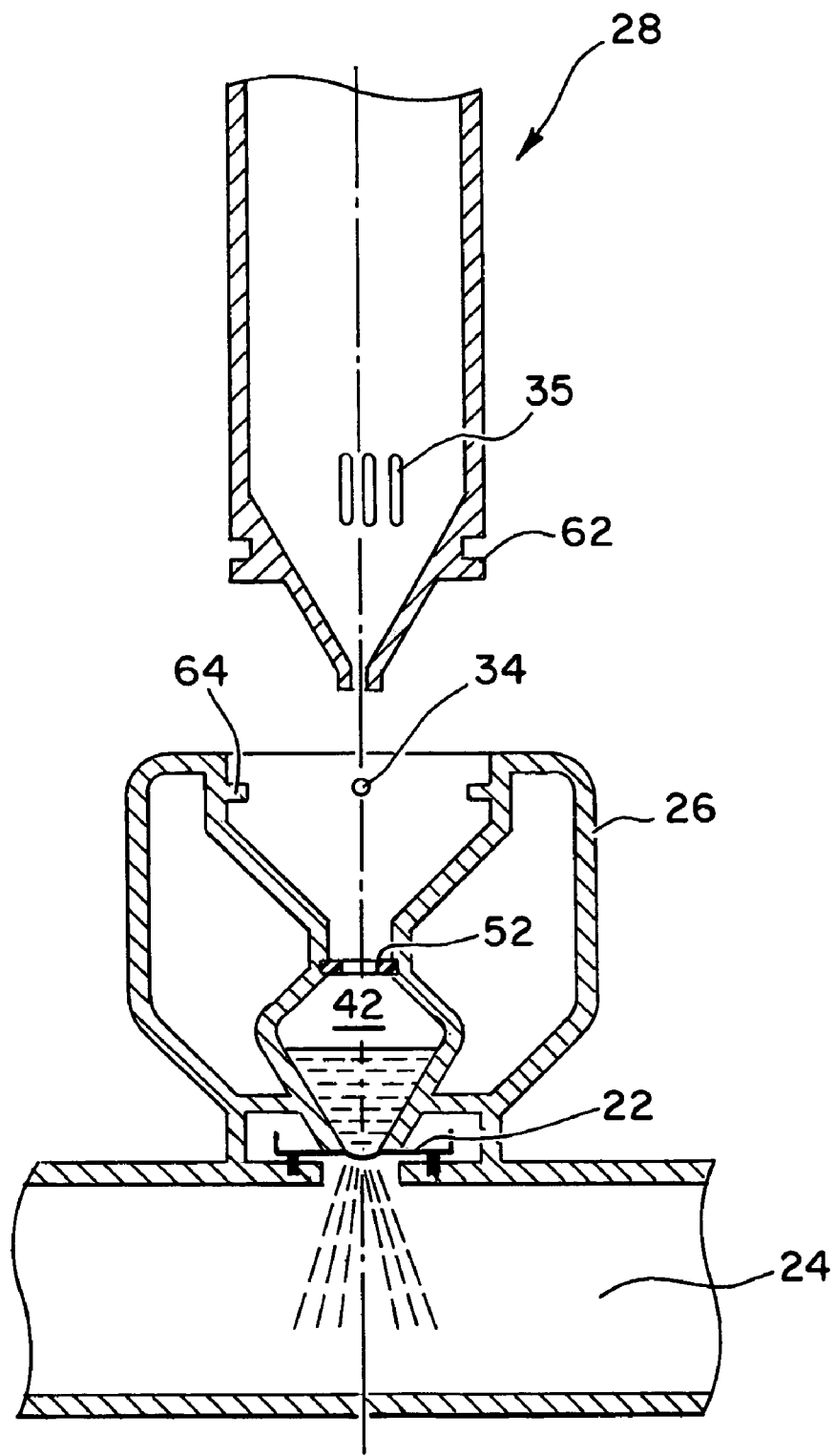
FIG. 9 is a cross sectional plan view illustrating another ampoule and feed system interface.

FIG. 9 illustrates one exemplary embodiment of an ampoule 28 having identification markers 35 that are disposed in a non-helical arrangement. As illustrated, ampoule includes a keying slot 62 adjacent a bottom end of ampoule 23 to allow the ampoule to be inserted into feed system interface 26. If keying slot 62 does not correspond with the keying tab 64 on the interface, the ampoule will be prevented from being seated within the interface and the liquid in the ampoule will be prevented from being delivered to reservoir 42. In situations where the keying slot matches the keying tab, as ampoule 28 is inserted axially into feed system and twisted to engage the keying slots with the keying tabs, the identification marker 35 will simultaneously pass across nebule sensor 34. The illustrated embodiment includes a bar code reader that reads a bar code identification marker, but it should be appreciated that the identification marker 35 and identification sensor 34 can include any of the other types of identification markers and sensors or their equivalents, as described above.

Figure 10:
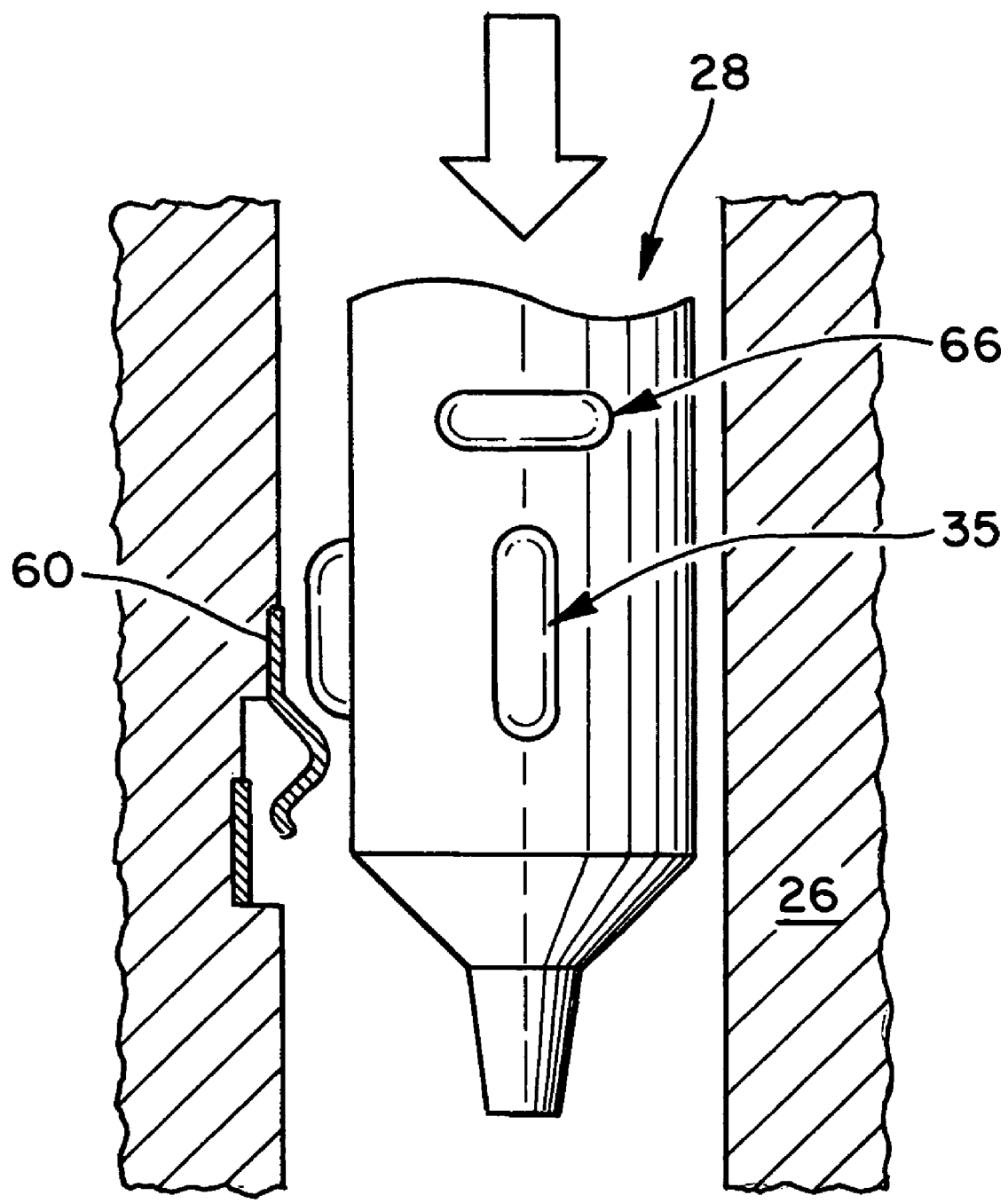
FIG. 10 is a plan view of an ampoule having an identification marker disposed in a non-helical configuration.

FIG. 10 illustrates an ampoule 28 that includes bump identification markers that are disposed on the ampoule such that axial insertion of the ampoule (without rotation) into the feed system interface 26 contacts the bump identification markers 35 against the electromechanical contacts 60. Ampoule 28 can include a retainer or click positive position feedback element 66, and/or alignment means for aligning the ampoule into the feed system.

Variations to the above description may be made in accordance with the present invention. For example, ampoule 28 can include other keying elements and/or orientation elements to ensure that the ampoule is properly oriented when it is inserted into the aerosolization device. A more detailed description of such keying elements and orientation elements can be found in co-pending U.S. patent application Ser. No. 09/812,755, filed Mar. 20, 2001, the complete disclosure of which was previously incorporated herein by reference. In such embodiments, the identification markers 35 can be disposed on the ampoule relative to such keying or orientation elements in any position in which the sensors can sense the markers and determine the type of medicament or drug that is disposed in the ampoule.

Methods of the present invention will now be described. In one method, the present invention identifies the contents of the nebule to improve the operation of the aerosol generator. As illustrated in FIG. 11, an aerosol generator is provided (Step 100) and a nebule is coupled to a nebule interface of the aerosol generator (Step 102). An identification marker on the nebule is read by the aerosol generator (Step 104) and the aerosol generator is operated according to an operation program based on the information read from the identification marker on the nebule (Step 106).

Typically, the aerosol generator is operated with a controller (FIG. 1). The controller typically includes a memory that stores a plurality of operation programs for delivering each of the compatible specific types of drugs or medication. After the identification marker is read by a sensor, the information is passed to the controller so that a correct operation program can be selected to operate the aerosol generator. The operation program can control the start and stop times of the aerosol generator, the aerosol production rate, the amplitude of vibration of the aerosolization element, the frequency of aerosolization, and the like.

It should be appreciated that, in addition to using the identification marker information to control the operation of the aerosol generator, the information from the identification marker may be used for other purposes. For example, as shown in FIG. 1, the systems of the present invention 20 may optionally include an output device 68, such as a printer, audio speaker, or LCD. When the identification information received by the sensor matches a code entry inside the controller memory, the drug name, dosage information, or other pertinent information can be made available to the user by displaying or announcing the information via the attached output devices. Additionally, the identification markers can be used for preventing the wrong drug from being administered to the patient by setting the aerosol generator controller to operate the aerosol generator only on the reception and identification of one or more particular drug codes/identification markers to the exclusion of others: e.g. one patient's nebulizer may be set to accept nebules containing, and coded for, drug A and drug B, while another patient's nebulizer may be set to only operate if a nebule contains, and is coded for, drug A.

Typically, the identification marker is positioned adjacent a sensor through use of a keying element on the nebule. The keying elements can interact with a corresponding keying feature on the aerosol generator interface to position the identification marker adjacent the sensor. In other methods, however, the keying elements on the nebule can be used to control the types of nebules that can be coupled to the aerosol generator system. In such methods, as shown in FIG. 12, a nebulizer system and a nebule comprising a nebule body with a keying element (e.g., threads, tabs, slots, and the like) are provided (Steps 110, 112). The nebule can be inserted into the housing. If the keying element is properly keyed with a housing of the nebulizer system, the nebule can access a reservoir of the system (Step 114). Thereafter, the liquid from the nebule will be transferred into the reservoir for aerosolization (Step 116). The aerosol generator can then be operated with a controller to aerosolize the liquid (Step 118).

The keying elements, identification markers, or both can be used to ensure that only nebules which are compatible with the feed system and aerosol generator are used. For example, as a first precaution, the aerosol generator systems of the present invention can include a keying feature that mates only with certain types of nebules. For example, nebules containing steroids may have a different keying element than nebules containing antibiotics. Therefore, patients using the aerosol generator only for steroidal delivery will be prevented from keying the nebule containing an antibiotic to the aerosol generator and inadvertently nebulizing the antibiotic, and vice versa.

Additionally or alternatively, the controller of each individual system can be programmed to only have available sequence delivery programs (which may be referred to as operation sequences, or algorithms for operation sequences) for selected medicants or drugs that are found in a library of codes and drugs in the controller memory. Thus, if the identification marker on a nebule that is coupled to the aerosol generator is not one of the drugs on the list stored in the controller memory, the controller will not deliver the aerosol to the patient. Optionally, the controller can provide an output informing the user that the installed nebule is incompatible with the system.

In other exemplary methods, the present invention can measure the characteristics of a persons inhaled breath, typically a tidal breath, to control the operation of the aerosol generator. As shown in FIG. 13, a person can take one or more breaths (Step 120) and the characteristics of the breath can be measured (Step 122). The breathing characteristics that can be measured include, but are not limited to, a breathing pattern, peak inspiratory flow rate, breathing rate, exhalation parameters, regularity of breathing, tidal volume, and the like and can estimate a user's tidal volume based on such information. The user can take another tidal breath and the aerosol generator can be operated based on the measured characteristics of the tidal breath (Step 124). It should be appreciated however, that instead of a tidal breath, the person can take other types of breath. Alternatively, the controller may base the timing of operation of the aerosol generator so that aerosol is generated at specific time periods within a breathing cycle, (Step 125, FIG. 13a). For example, the controller may operate the aerosol generator for the first 50 percent of inspiration. Alternatively, the controller may operate the aerosol generator to generate aerosol after a portion of inhalation has taken place and to cease producing aerosol after another portion of inhalation has taken place. For example, the controller may cause aerosol to be generated beginning after 20% of the inspiration has taken place and cause aerosol production to cease after 70% of inspiration has taken place. The controller may cause aerosol production to start after, for example, after 90% of exhalation has taken place and, for example, cause aerosol production to stop after 30% of the following inspiration has taken place. By controlling the specific timing within the breathing cycle that aerosolized medication is provided into the breathing circuit, greater efficiency of drug administration can be achieved. With reference to FIGS. 15a-15c, for example, continuous aerosolization may yield only about 10% to about 15% efficiency (FIG. 15a), aerosolization during the entire inhalation phase of the breathing cycle may yield about 15% to about 25% efficiency (FIG. 15b), and delivery during a predetermined portion of the inhalation phase beginning, for example, at the onset of inhalation, may provide a drug yield between about 60% to about 80% efficacy (FIG. 15c). Accordingly, the present invention, by controlling delivery to a predetermined percentage of the breathing cycle, such as a predetermined percentage of the inhalation phase of the breathing cycle, provides far greater efficiency than either continuous delivery or delivery during the entire inhalation phase. Further, and surprisingly, the percentage of increase in efficiency in delivery for such a predetermined portion of the inhalation phase (FIG. 15c) over delivery during the entire inhalation phase (FIG. 15b) is itself far greater than the increase in efficiency of delivery during the inhalation phase (FIG. 15b) over simply continuously providing aerosol (FIG. 15a).

By utilizing an aerosol generator that produces aerosol by the electric powering a vibratable member that causes an aperture plate to eject liquid at one face thereof, through its apertures, as a mist from the other face thereof, as generally described above (and as described generally in U.S. Pat. No. 5,164,740; 5,938,117; 5,586,550; 5,758,637, 6,085,740; and 6,235,177, the complete disclosures of which are, and have been above, incorporated herein by reference), the starting and stopping of aerosol generation may be controlled on the level of accuracy of microseconds or milliseconds, thus providing accurate dosing. The timing of aerosol generation can be done based solely on a predetermined timing within a breathing cycle, on timing in conjunction with the length of a prior breath or portions thereof, on other breathing characteristics, on particular medication being administered, or a combination of any of these criteria (Step 135, FIG. 13*b*).

Figure 16A:
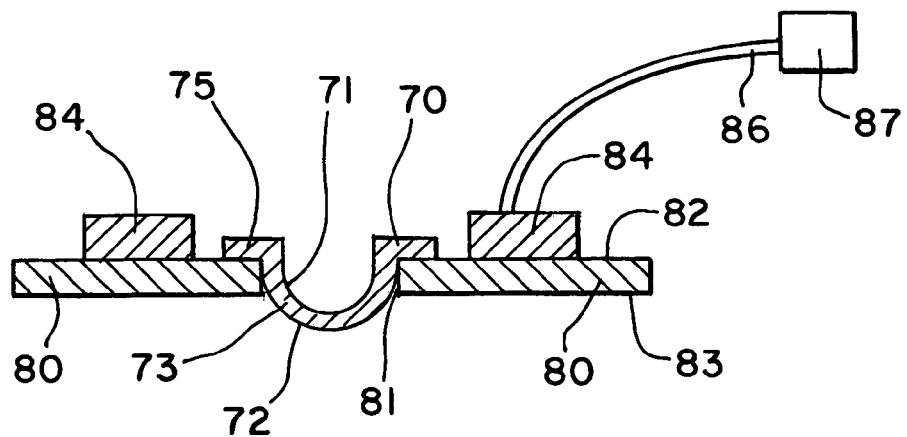
FIG. 16a is a schematic cross-sectional representation of an aerosol generator in accordance with the present invention.
Figure 16B:
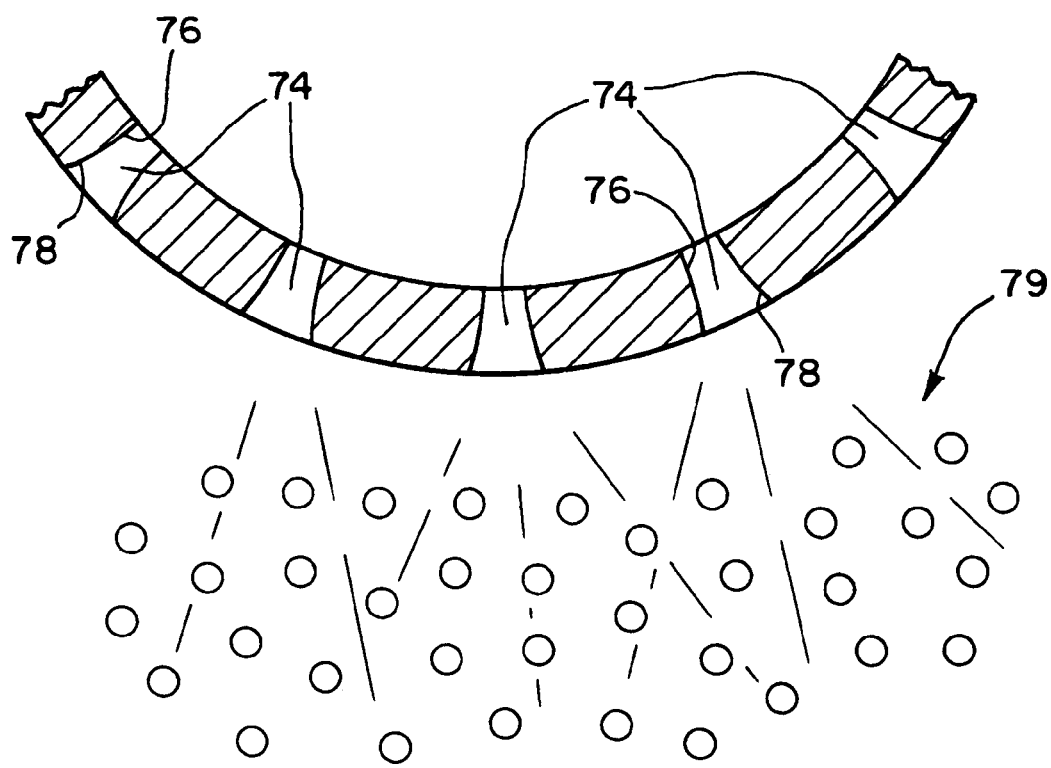

The aerosolization element may be constructed of a variety of materials, comprising metals, which may be electroformed to create apertures as the element is formed, as described, for example, in U.S. Pat. No. 6,235,177 assigned to the present assignee and incorporated by reference herein in its entirety. Palladium is believed to be of particular usefulness in producing an electroformed, multi-apertured aerosolization element, as well as in operation thereof to aerosolize liquids. Other metals that can be used are palladium alloys, such as PdNi, with, for example, 80 percent palladium and 20% nickel. Other metals and materials may be used without departing from the present invention. The aerosolization element 70 (referring now to FIGS. 16*a* and 16*b*) may be configured to have a curvature, as in a dome shape, which may be spherical, parabolic or any other curvature. The aerosolization element may be formed to have a dome portion 73 over its majority, and this may be concentric with the center of the aerosolization element, thus leaving a portion of the aerosolization element that is a substantially planar peripheral ring portion 75. The aerosolization element has a first face 71, a second face 72 and a plurality of apertures 74 (FIG. 16*b*) therethrough. The first face 71 may comprise the concave side of the dome portion 72 and the second face 72 may comprise the convex side of the dome portion 72 of the aerosolization element 70. The apertures may be tapered to have a narrow portion 76 at the first face 71 and a wide portion 78 at the second face 72 of the aerosolization element 70. Typically, a liquid will be plated at the first face of the aerosolization element, where it can be drawn into the narrow portion 76 of the apertures 74 and emitted as an aerosolized mist or cloud 79 from the wide portion 78 of the apertures 74 at the second face 72 of the aerosolization element 70.

The aerosolization element may be mounted on an aerosol actuator 80, which defines an aperture 81 therethrough. This may be done in such a manner that the dome portion of the aerosolization element protrudes through the aperture 81 of the aerosol actuator 80 and the substantially planar peripheral ring portion 74, on the second face 72 of the aerosolization element 70 abuts a first face 82 of the aerosol actuator 80. A vibratory element 84 may be provided, and may be mounted on the first face 82 of the aerosol actuator 80, or alternatively may be mounted on an opposing second face 83 of the aerosol actuator 80. The aerosolization element may be vibrated in such a manner as to draw liquid through the apertures 74 of the aerosolization element 70 from the first face to the second face, where the liquid is expelled from the apertures as a nebulized mist. The aerosolization element may be vibrated by a vibratory element 84, which may be a piezoelectric element. The vibratory element may be mounted to the aerosol actuator, such that vibration of the vibratory element may be mechanically transferred through the aerosol actuator to the aerosolization element. The vibratory element may be annular, and may surround the aperture of the aerosol actuator, for example, in a coaxial arrangement. In some embodiments of the present invention, the aerosolization element or the aerosol generator comprising the aerosolization element 70, the aerosol actuator 80 and the vibratory element 86 may be replaced with a respective assembly that has apertures of a different size, such as a different exit diameter, to produce a mist having a different aerosol particle size. A circuitry 86 may provide power from a power source. The circuitry may include a switch that may be operable to vibrate the vibratory element and thus the aerosolization element, and aerosolization performed in this manner may be achieved within milliseconds of operation of the switch. The circuitry may include a controller 87, for example, a microprocessor that can provide power to the vibratory element 84 to produce aerosol from the aerosolization element 70 within milliseconds or fractions of milliseconds of a signal to do so. For example, aerosol production may begin within about 0.02 to about 50 milliseconds of such a signal and may stop within about 0.02 to about 50 milliseconds from the cessation of a first signal or a second signal either of which may act as a trigger to turn of aerosolization. Similarly, aerosol production may begin and end within about 0.02 milliseconds to about 20 milliseconds of such respective signaling. Likewise, aerosol production may begin and end within about 0.02 milliseconds to about 2 milliseconds of such respective signaling. Further, this manner of aerosolization provides full aerosolization with a substantially uniform particle size of low velocity mist 79 being produced effectively instantaneously with operation of the switch.

Figure 17:
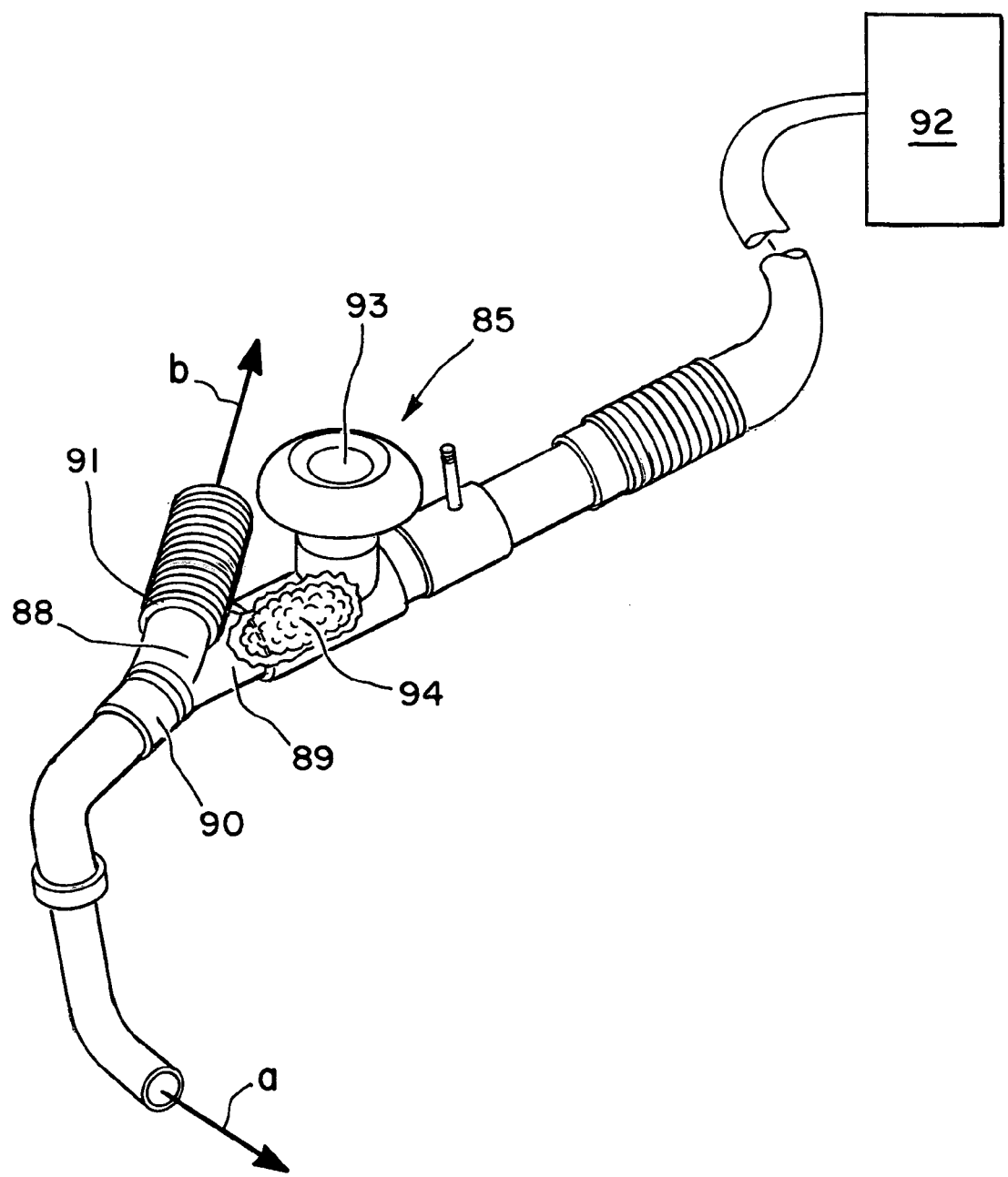
FIG. 17 is a schematic perspective view of a nebulizer incorporated into a ventilator breathing circuit in accordance with the present invention.

With reference to FIG. 17, a nebulizer 85, which may have a top portion 93 through which liquid (either directly or within a nebule) may be provided, in accordance with the present invention may be incorporated into a ventilator breathing circuit of a ventilated patient. The breathing circuit may comprise a "Y" connector 88, which may in turn have an inlet portion 89, an endotracheal tube portion 90 and an outlet portion 91. The inlet portion 89 carries air provided from the ventilator 92 toward the patient. The endotracheal tube portion 90 of the Y connector 88 carries the incoming air to the patient's respiratory tract; this direction is represented by arrow a. The endotracheal tube portion 90 also carries the patient's exhalation to the outlet portion 91 of the Y connector 88, and the outlet portion may lead to an exhaust, represented by arrow b, to remove the patient's exhalation from the system. The nebulizer 85 of the present invention aerosolization element generates an aerosol cloud 94 that remains substantially within the inlet portion 89 of the Y connector 88 when there is no inspiratory air flowing through the inlet portion, by virtue of the aerosolization element, as described above, producing a low velocity mist. In this manner, aerosol that is generated when there is no inhalation air being provided will not be carried out through the outlet portion 91 of the Y connector and lost to the ambient environment. Accordingly, a dose of aerosolized medication may be preloaded, i.e., produced and placed substantially within the inlet portion 89 prior to an inhalation phase being sent by the ventilator 92. In this manner, such medication can be swept into a patient's respiratory system at the very start of the inhalation cycle. This may be of particular benefit in the case of neonatal patients and in other instances in which only the initial blast of inhalation phase will reach the target portion of the respiratory system.

The switch, described above, may be operable by a pressure transducer, which may be positioned in the mouthpiece of the nebulizer. The pressure transducer may be in electrical communication with the circuitry, and a microprocessor may also be in electrical communication with the circuitry, and the microprocessor may interpret electrical signals from the pressure transducer, and may also operate the switch to begin aerosolization. In this manner, nebulization can begin substantially instantaneously with the inhalation of a user upon the mouthpiece. An example of such a sensor switch can be found in co-assigned and co-pending U.S. application Ser. No. 09/705,063 assigned to the present assignee, the entire content of which is hereby incorporated herein by reference.

Another transducer may be used to sense the absence or presence of liquid in the reservoir, by sensing, for example, a difference between vibration characteristics of the aerosolization element, such as, for example, differences in frequency or amplitude, between wet vibration and substantially dry vibration. In this manner, the circuitry, may, for example by way of the microprocessor, turn the vibration off when there is essentially no more liquid to aerosolize, i.e., when the end of the dose has been achieved, thus minimizing operation of the aerosolization element in a dry state. Likewise, the switch may prevent vibration prior to delivery of a subsequent dose into the reservoir. An example of such a switch is shown in co-assigned and co-pending U.S. application Ser. No. 09/805,498, the entire content of which is hereby incorporated herein by reference.

As shown schematically in FIG. 14, in exemplary embodiments, the aerosol generator controllers of the present invention can be coupled to both a nebule identification sensor and a breathing characteristic sensor so as to identify the liquid that is delivered to the aerosol generator and to monitor the breathing characteristics of the patient (Steps 130 to 140). In such embodiments, the aerosol generator can be operated (and a pre-programmed delivery program can be selected) to run the aerosol-generator, based at least in part on the information obtained from the identification sensor and breathing characteristic sensor (Step 140).

If it is known what type of medication or drug is being delivered, the controller can select the best time during the patient's breathing cycle to deliver the aerosol, based upon a predetermined regimen for that drug that is stored in memory. As an additional benefit, an estimate of the patient's age and/or distress can be made, for example, by measuring the tidal volume and breathing rate. Such measurements can influence the efficiency requirements of the dose per breath. These or other variables can be used in establishing various regimes for aerosol delivery, in particular delivery into the breathing circuit of a ventilator. These regimes can be stored in memory and then accessed by the controller as appropriate for a given patient condition.

For example, for a bronchodilator the best time to delivery may be half way through the inhalation phase of a breath when impaction would be reduced since inhalation flows are reducing. For steroids, it may be best to deliver towards the end of the inhalation phase of a breath. For antibiotics, it may be best to slightly pre-load, i.e. deliver aerosol during the exhalation phase, or deliver right at the start of the breath. For example, antibiotics may be delivered at the beginning of a ventilator provided inhalation, and the aerosol delivery may stop after a predetermined percentage of the inhalation has been provided. One class of antibiotics that may be administered in accordance with the present invention is the class known as the aminoglycoside class of antibiotics. This class of antibiotics has typically been administered intravenously, however, such delivery may have unwanted side effects, which may be systemic. An object of the present invention is the administration of antibiotics, such as aminoglycosides including amikacin by delivering it in aerosolized form into the breathing circuit of a patient on a ventilator. In this manner, amikacin can be used to treat pulmonary infection conditions that typically arise when patients are mechanically ventilated, and the amikacin, or other aminoglycoside or other antibiotic, can be delivered directly to the target of treatment, the pulmonary tract, avoiding side effects that may otherwise arise from intravenous administration. Further, because of the great cost of such drugs, far greater efficiency is achieved through this pulmonary delivery. As noted above, with reference to FIG. 15c, delivery of aerosol during a beginning percentage of the inhalation phase of a breathing cycle may yield up between about 60% and about 80% efficiency, an this is significantly higher than efficacy of continuous aerosolization or aerosolization for an entire inhalation phase of an inhalation cycle.

Figure 19:
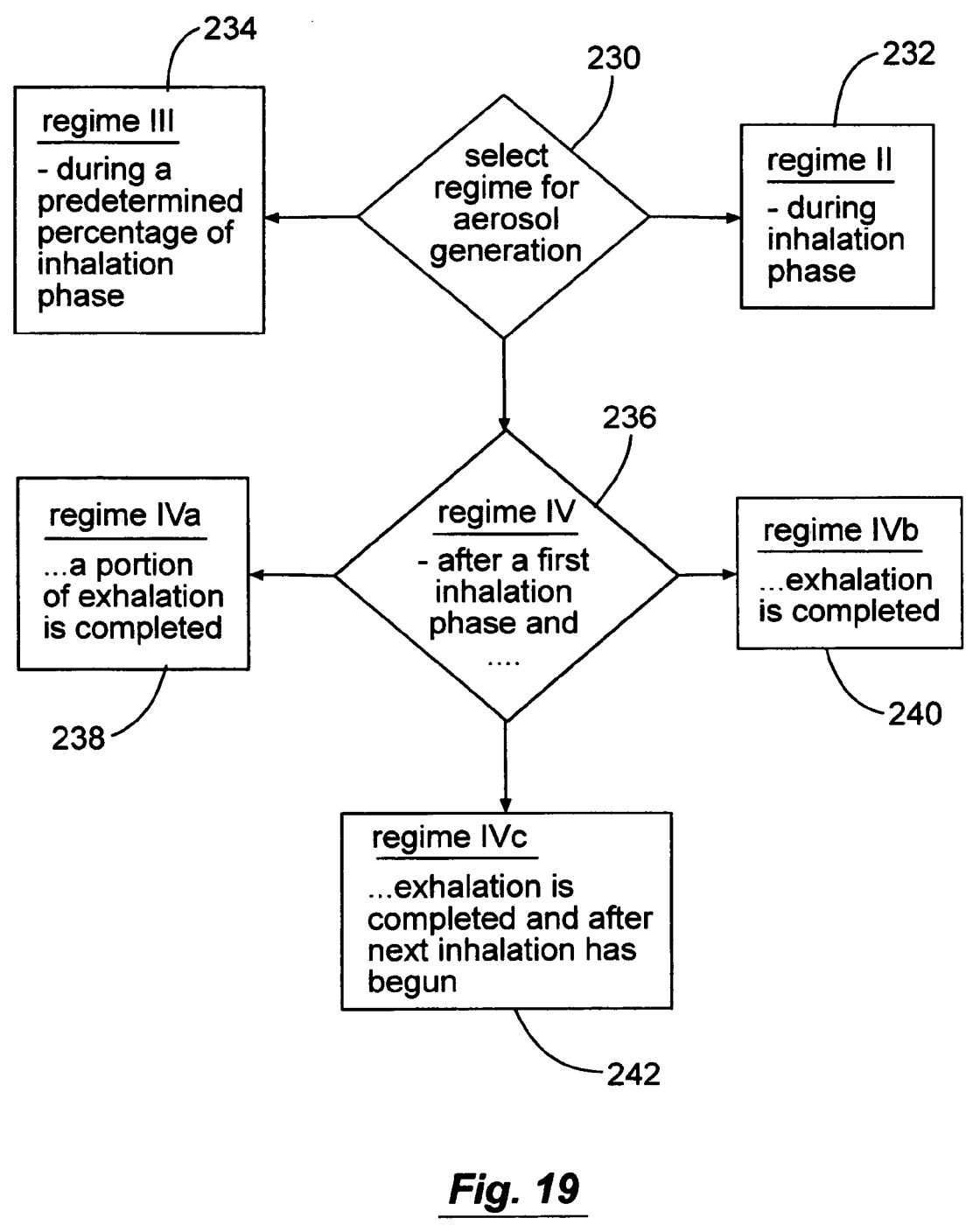

As described above, various regimes of aerosolization can be followed, depending on the situation. For example, in FIG. 18, a selection between a first, second and third regime is shown. A regime may be selected manually or automatically, for example, through the application of an algorithm that selects an operation program based on information that is either input or stored. For manual selection, a user may operate a mechanical switch to select a regime, or may enter such a selection into an electronic input device, such as a keyboard. Alternatively, the controller may automatically choose a regimen, as described above, by matching a drug code on a drug nebule with a library of drug-regimen combinations. (It should be noted that in FIGS. 18, 19 and 20, schematic flow charts of operation sequence algorithms are depicted. Although items therein will be referred to as steps for ease of discussion, they refer more broadly herein to states of operations or modalities in which a system may exist or cycle through. Steps depicted in a rectangle are essentially states of operation, actions or modalities. Steps depicted in diamonds indicate either a selection or the continuance of the previous state of operation, action or modality until a predetermined condition is satisfied. Two successive diamonds refer to satisfaction of a first condition and of a second condition respectively, the second of which may be a subset of the first.)

In step 200, a choice is made to follow a particular regime. In this case, regime I is a regime in which aerosol is generated continuously (step 202). Regime II provides aerosol generation during the inhalation phase only (step 204). In this case, in step 206, aerosol generation is set to start at the start of the inhalation phase and, in step 208, aerosol generation is set to stop when the inhalation phase stops. In step 210, aerosol generation begins at the start of the inhalation phase. In step 212, when the inhalation phase ends, aerosol generation stops (step 214).

Regime III provides for inhalation during a predetermined percentage of the inhalation phase (step 216). A predetermined percentage of an inhalation (or exhalation) phase may be based on a measured time from a discrete point in the ventilator cycle, such as the instantaneous commencement of inspiratory air generation by the ventilator. Alternatively, such predetermined percentage may be based on the time interval between successive discrete points in the ventilator, such as successive commencements of successive inhalation air generation by the ventilator. Alternatively, such percentages may be based upon air pressure in the ventilator circuit, or any other parameter. With respect to Regime III, in this case, in step 218, a first predetermined point is set to correspond with the completion of a first predetermined percent of the inhalation. In step 220, a second predetermined point is set to correspond to a second predetermined percent of inhalation percent being completed. For example, as described above, the first predetermined point may correspond to 20% of the inhalation phase being completed, and the second predetermined point may correspond to a point at which 70% of that same inhalation has taken place. In step 222, aerosol generation begins at the first predetermined point in the inhalation phase. In step 224, when the second predetermined point is reached, the controller carries out step 214 and stops the aerosol generation.

Similarly, as noted above, other regimes may be followed, for example, in which aerosol generation begins during the inhalation phase and ends during the exhalation phase, or begins during exhalation and ends during that exhalation, or begins during exhalation and ends in the subsequent breath cycle, for example, at a predetermined point in the subsequent inhalation phase. Accordingly, turning to FIG. 19, a selection may be made, at step 230, between regimes II (step 232) and III (step 234) as described above, and another regime, regime IV (steps 236-242), which is also available for selection. In regime IV, aerosol generation may begin at a first predetermined point (step 236), and this first predetermined point may be after a predetermined percentage of the inhalation phase has taken place, or it may be a predetermined point after the inhalation phase has been completed. For example, this point may be a predetermined point after a predetermined percent of the exhalation phase has taken place, or may be a predetermined point prior to the start of the subsequent inhalation phase. Aerosol generation may stop during exhalation (regime Iva, step 238), at the completion of exhalation (regime UVb, step 240), or aerosol generation may continue into the next breath cycle (regime UVc, step 242), and stop, for example, after a predetermined point during the subsequent inhalation phase.

In this example, with the controller having a selection choice between operation sequences corresponding to regimes II, III and IV, schematic representation of the operation sequences are shown in FIG. 20. In step 250, a regime is selected. In step 252, the aerosol generator controller selects an operation sequence based on selected regime. In step 254, the controller receives a signal indicating that ventilator has begun to supply an inhalation phase. The signal, as described above, may be a signal provided directly by the ventilator. Alternatively, the signal may be provided by a sensor, and such sensor may sense the commencement of an inhalation phase provided by the ventilator, as described above, by sensing a pressure change in the breathing circuit. In step 256, the controller carries out selected operation sequence. In the case of regime II (step 258), the controller turns on aerosol generator upon commencement of inhalation phase provided by the ventilator. The controller continues to operate the aerosol generator until a point at which the inhalation phase completed (step 260). In step 262, controller turns off aerosol generator.

In the case of regime III, the controller does not take any action to begin aerosol generation, until a predetermined point in the inhalation phase, corresponding to a percentage of the inhalation phase being completed (step 264). In step 266, at a predetermined point in the inhalation phase, the controller turns on aerosol generator. In step 268, aerosol generation continues until a second predetermined point inhalation phase, corresponding to a second percentage point of completion of the inhalation phase. At this point, the controller carries out step 262 and turns off aerosol generator. With respect to regime IV, aerosol generation begins after a predetermined point of completion of the inhalation phase (step 264) and this point may be predetermined to occur after the inhalation phase has been completed and the exhalation phase has begun (step 270). In step 272, the controller turns the aerosol generator on to begin aerosolization. Variations can be made as to the point at which the aerosol generation is turned off. If it is desired that aerosol generation be completed before the completion of the exhalation phase (regime IVa), then aerosol generation may continue until a predetermined point prior to the subsequent inhalation (step 276). Alternatively, it may be desirable to continue aerosolization until the end of exhalation, which may correspond to the point of commencement of the subsequent inhalation, as in regime UVb (step 278). Alternatively, it may be desired to follow a regimen such as regime IVc, where aerosol generation continues through into the subsequent breath cycle (step 280), until, for example, a predetermined percent of the subsequent inhalation phase has been completed (step 282). In these regimes, aerosolization will continue until the satisfaction of these conditions (step 276 for regime UVa, step 278 for regime IVb or step 282 for regime UVc), at which point the controller carries out step 262 and stops the aerosol generator. The process may continue with the next signal indicating that the ventilator has begun to provide an inhalation phase, step 254.

Further, the choice of which operating sequence to follow may rely at least in part on the identity of a drug to be administered, which information can be considered by the controller as described above. In addition, it should be appreciated that modifications may be made to these examples without departing from the present invention. For example, a system may be configured, or a method may be carried out, to be able to select more than three initial regimes to follow. For example, regimes I, II, III and IV as described above may be simultaneously selectable. Further, various steps may be altered; for example, some steps may not be discrete steps. Thus, step 256 may not be a discrete step but rather the following of an operation sequence according to a selected regime. Similarly, the order of the steps may be changed, such as the controller may select an operating sequence (step 252) after receiving a signal that the ventilator has commenced to provide an inhalation phase (step 254). Steps may also be combined, such as, for example, in regime IV steps 264 and 270 may be combined as a single step, as these two steps represent successive criteria for the determining a single first predetermined point has been met. Likewise, step 274 may be combined with steps 276, 278 or 280, as step 274 is the predicate for the condition test specified in each of the other successive tests, steps 276, 278 or 280. The algorithm examples may be altered to form other operating sequences. For example, an operating sequence may call for the controller to start aerosol generation at the start of the inhalation cycle provided by the nebulizer, as in regime II, at step 258, and turn off the aerosol generator at a point at which a predetermined percentage of the inhalation phase has been completed, as in regime III, step 268 (and step 262). In a similar manner, other criteria may be used to trigger the turning on or off of the aerosol generator. For example, as described above, the start of aerosolization may be triggered by the sensing of a particular pressure or change in pressure in the ventilator circuit, and may end by following the turning off sequence of regimes III (steps 268 and 262) or IV (steps 274, 276, 278 or 280 and 282, followed by step 262, as described above.

Figure 21:
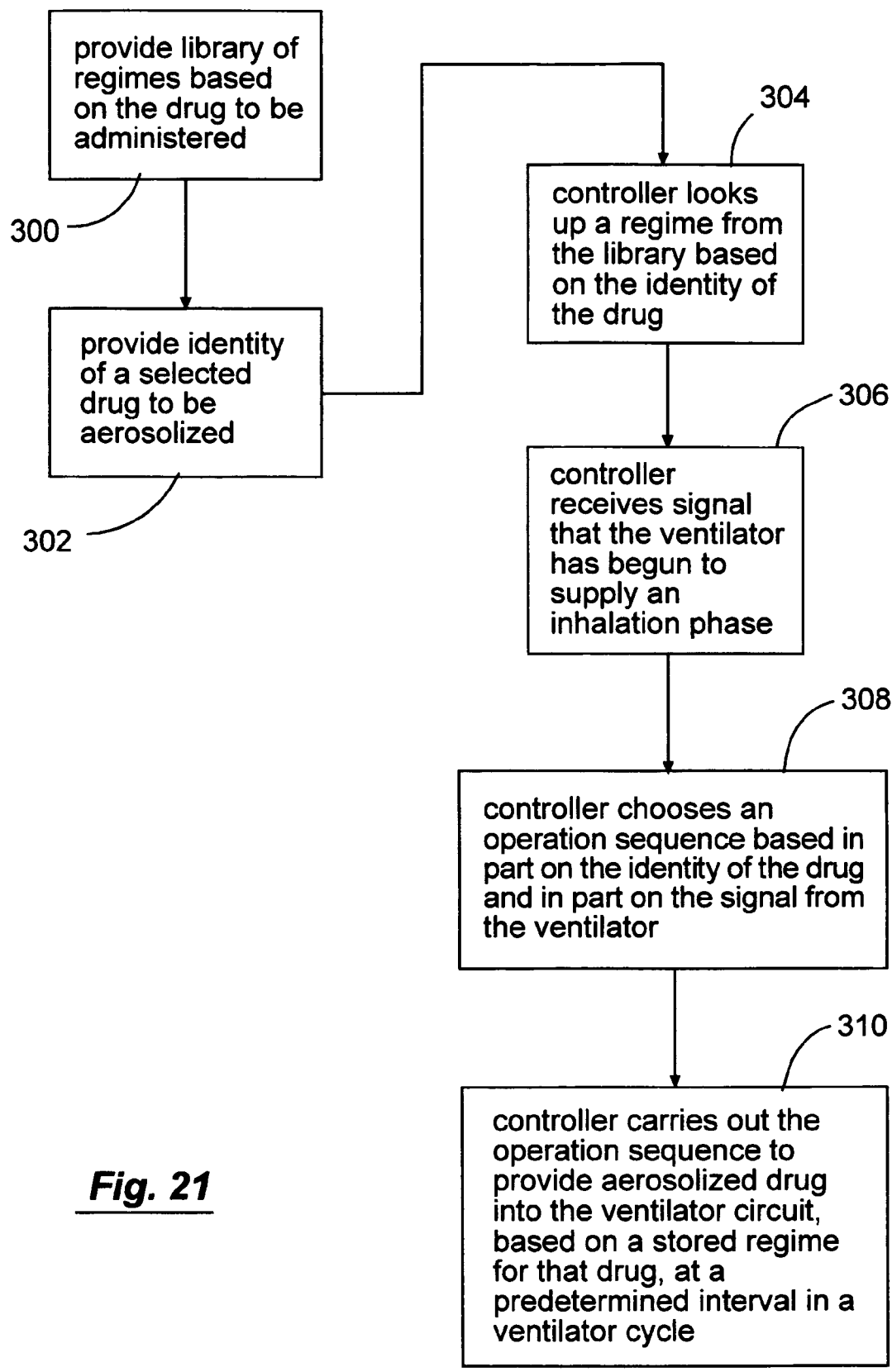
FIG. 21 is a schematic representation of an algorithm by which an operating sequence may be chosen base on the combination of a plurality of independent sets of information.

FIG. 21 is a schematic representation of an algorithm by which an operating sequence, for providing nebulized drug to a patient receiving air from a ventilator, may be chosen based on the combination of a plurality of independent sets of information, in this case, drug identity and a signal from the ventilator. In step 300, a library of drug regimes is provided, the library based on various drugs that may be administered. In step 302, the identity of a particular drug is provided to the system, and this may be provided, as described above, by a marker on a nebule containing the drug, the marker being read by the system. In step 304, the controller looks up a regime from the library of stored regimes to select a regime based on the particular drug to be administered. In step 306, the controller receives a signal from the ventilator. In step 308, the controller then chooses an operation sequence based in part on the drug identity and drug regime and in part on the independent information provided by the signal from the ventilator. In step 310, the controller carries out the operation sequence, which may be producing aerosol at a predetermined interval in the ventilation cycle based on the drug and the regime provided for the drug factored in with the inhalation cycle of the ventilator. These descriptions are illustrative, and accordingly, the order of the steps may be altered, and other variations, additions and modifications, as described above, may be made still in accordance with the present invention.

While all the above is a complete description of the preferred embodiments of the inventions, various alternatives, modifications, and equivalents may be used. Accordingly, although the foregoing invention has been described in detail for purposes of clarity of understanding, it will be obvious that certain modifications may be practiced within the scope of the appended claims.

What is claimed is:

1. A system for providing nebulized fluid to a ventilated patient, comprising:
    a ventilator,
    a breathing circuit,
    a vibratory aerosolization element having a first face, a second face and a plurality of apertures therethrough;
    a controller configured to control vibration of the vibratory aerosolization element,
    wherein the controller may be configured to vibrate the vibratory aerosolization element during a selected interval of a breathing cycle.

2. The system of claim 1, wherein the selected interval is based on a predetermined point of the breath cycle provided by the ventilator.

3. The system of claim 2, wherein the predetermined point is the commencement of an inhalation phase provided by the ventilator.

4. The system of claim 2, wherein the interval begins at a first predetermined point in the breathing cycle and ends at a second predetermined point in the breathing cycle.

5. A system for providing nebulized fluid to a patient receiving air from a ventilator, comprising:
    a breathing circuit comprising a Y connector, the Y connector comprising an inlet portion, an endotracheal tube portion and an outlet portion;
    a nebulizer positioned to provide nebulized fluid into the inlet portion of the Y connector, the nebulizer comprising: a vibratory aerosolization element having a first face, a second face and a plurality of apertures therethrough;
    wherein the vibratory element may be caused to vibrate at least in part by an electrical signal in a manner so as to draw fluid into the apertures at the first face thereof and emit the fluid as a low velocity nebulized cloud from the second face, and wherein the force of the emitted cloud is small enough that substantially no aerosol is lost though the outlet portion when there is no inspiratory flow through the inlet portion.

6. The apparatus of claim 5, wherein substantially no aerosol travels into the endotracheal tube portion of the Y connector when there is no inspiratory flow though the inlet portion.

7. A system for providing nebulized fluid to a patient receiving air from a ventilator, comprising:
    a breathing circuit comprising a Y connector, the Y connector comprising an inlet portion, an endotracheal tube portion and an outlet portion;
    a nebulizer positioned to provide nebulized fluid into the inlet portion of the Y connector, the nebulizer comprising: a vibratory aerosolization element having a first face, a second face and a plurality of apertures therethrough;
    wherein the vibratory element may be caused to vibrate at least in part by an electrical signal in a manner so as to draw fluid into the apertures at the first face thereof and emit the fluid as a low velocity nebulized cloud from the second face, and wherein the force of the emitted cloud is small enough that substantially all of the cloud may travel no further than the inlet portion of the Y connector when there is no inspiratory flow through the inlet portion.

8. A method of providing nebulized fluid to a patient receiving air from a ventilator, comprising:
    providing a ventilator,
    providing a breathing circuit to connect the ventilator to a patient, the breathing circuit comprising a Y connector, the Y connector comprising an inlet portion, an endotracheal portion and an outlet portion,
    providing a nebulizer positioned to provide aerosol into the inlet portion of the Y connector, the nebulizer comprising a vibratory aerosolization element, the vibratory aerosolization element operable in part by an electronic signal;
    providing an electronic signal that causes the aerosolization element to vibrate in such a manner as to deliver a cloud of mist into the inlet portion of the inlet portion during an interval in which there is substantially no inhalation flow through the inlet portion, such that the cloud remains substantially within the inlet portion;
    providing an inhalation flow from the ventilator in such a manner as to sweep substantially the entire cloud of mist through the endotracheal tube portion to the patient substantially upon the commencement of the inhalation flow.

9. A method of providing nebulized fluid to a neonatal patient receiving air from a ventilator, comprising:
    providing a ventilator,
    providing a breathing circuit to connect the ventilator to a patient, the breathing circuit comprising a Y connector, the Y connector comprising an inlet portion, an endotracheal portion and an outlet portion,
    providing a nebulizer positioned to provide aerosol into the inlet portion of the Y connector, the nebulizer comprising a vibratory aerosolization element, the vibratory aerosolization element operable in part by an electronic signal;
    providing an electronic signal that causes the aerosolization element to vibrate in such a manner as to deliver a cloud of mist into the inlet portion of the inlet portion during an interval in which there is substantially no inhalation flow through the inlet portion, such that the cloud remains substantially within the inlet portion;
    providing an inhalation flow from the ventilator in such a manner as to sweep substantially the entire cloud of mist through the endotracheal tube portion to the patient substantially upon the commencement of the inhalation flow.

10. A system for providing aerosol into a ventilator circuit, comprising;
    a ventilator capable of providing at least one cycle of inhalation air;
    a ventilator circuit comprising an inhalation tube, and exhalation tube and an intubation tube, and a Y connector therebetween;

a sensor configured to monitor a point within an inhalation cycle of the ventilator;

a nebulizer comprising a microprocessor, the microprocessor configured to calculate an inhalation profile based on the sensed point of operation of the ventilator, the microprocessor further configured to follow at least one algorithm for operating the nebulizer based on an inhalation profile, wherein the algorithm is configured to provide a point for the commencement of aerosolization and a point for the cessation of aerosolization.

11. The system of claim 10, wherein the of aerosolization and the point for cessation of aerosolization are not designed to coincide with the commencement of an inhalation phase and the cessation of an inhalation phase of an inhalation cycle provided by the nebulizer.

12. The system of claim 10, wherein the point for commencement of aerosolization and the point for cessation of aerosolization are not designed to coincide with the commencement of an exhalation phase and the cessation of an exhalation phase of an inhalation cycle provided by the nebulizer.

13. The system of claim 10, wherein the point for commencement of aerosolization and the point for cessation of aerosolization are chosen to maximize actual inhalation of aerosolized liquid.

14. The system of claim 13, wherein the point for commencement of aerosolization is a point following the completion of a predetermined portion of the inhalation phase of the inhalation cycle.

15. The system of claim 14, wherein the point for cessation of aerosolization is a point prior to a predetermined portion of the inhalation phase of the inhalation cycle has occurred.

16. The system of claim 13, wherein the point for cessation of aerosolization is a point following the completion of a predetermined portion of the subsequent exhalation phase of the inhalation cycle.

17. The system of claim 13, wherein the point for commencement of aerosolization is a point following the completion of a predetermined portion of the exhalation phase of the inhalation cycle.

18. The system of claim 17, wherein the point for cessation of aerosolization is a point following the completion of a predetermined portion of the exhalation phase of the inhalation cycle.

19. A method for providing a nebulized fluid to a ventilated patient, the method comprising:

providing a ventilator having a breathing circuit;

vibrating an aerosolization element in the presence of a fluid, wherein the aerosolization element includes a plurality of apertures that nebulize the liquid while the aerosolization element is vibrating;

introducing the nebulized liquid into the breathing circuit; and controlling vibration of the aerosolization element during a certain interval of a breathing cycle.

20. The system of claim 1, wherein the fluid comprises an antibiotic that is selected to treat a pulmonary infection resulting from mechanical ventilation, and wherein the interval is selected based on the antibiotic.

21. The system of claim 20, wherein the antibiotic is an aminoglycoside.

22. The system of claim 21, wherein the aminoglycoside is amikacin.

23. The apparatus as in claim 5, wherein the fluid comprises an antibiotic that is selected to treat a pulmonary infection resulting from mechanical ventilation.

24. The apparatus as in claim 23, wherein the antibiotic is an aminoglycoside.

25. The apparatus as in claim 24, wherein the aminoglycoside is amikacin.

26. The apparatus as in claim 7, wherein the fluid comprises an antibiotic that is selected to treat a pulmonary infection resulting from mechanical ventilation.

27. The apparatus as in claim 26, wherein the antibiotic is an aminoglycoside.

28. The apparatus as in claim 27, wherein the aminoglycoside is amikacin.

29. The method as in claim 8, wherein the fluid comprises an antibiotic that is selected to treat a pulmonary infection resulting from mechanical ventilation.

30. The method as in claim 29, wherein the antibiotic is an aminoglycoside.

31. The method as in claim 30, wherein the aminoglycoside is amikacin.

32. The method as in claim 9, wherein the fluid comprises an antibiotic that is selected to treat a pulmonary infection resulting from mechanical ventilation.

33. The method as in claim 32, wherein the antibiotic is an aminoglycoside.

34. The method as in claim 33, wherein the aminoglycoside is amikacin.

35. The method as in claim 8, wherein the mist comprises an antibiotic that is selected to treat a pulmonary infection resulting from mechanical ventilation.

36. The method as in claim 35, wherein the antibiotic is an aminoglycoside.

37. The method as in claim 36, wherein the aminoglycoside is amikacin.

38. The method of claim 19, wherein the fluid is an antibiotic that is selected to treat a pulmonary infection resulting from mechanical ventilation.

39. The method of claim 38, wherein the antibiotic is an aminoglycoside.

40. The method of claim 39, wherein the aminoglycoside is amikacin.

* * * * *